(12) United States Patent
Yadav et al.

(10) Patent No.: US 8,148,121 B2
(45) Date of Patent: Apr. 3, 2012

(54) Δ6 DESATURASES AND THEIR USE IN MAKING POLYUNSATURATED FATTY ACIDS

(75) Inventors: Narendra S. Yadav, Wilmington, DE (US); Zhixiong Xue, Chadds Ford, PA (US); Quinn Qun Zhu, West Chester, PA (US); Hongxiang Zhang, Chadds Ford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 314 days.

(21) Appl. No.: 12/512,429

(22) Filed: Jul. 30, 2009

(65) Prior Publication Data
US 2010/0041113 A1 Feb. 18, 2010

Related U.S. Application Data

(60) Provisional application No. 61/085,482, filed on Aug. 1, 2008.

(51) Int. Cl.
*C12P 7/64* (2006.01)
*C12N 9/02* (2006.01)
*C12N 1/20* (2006.01)
*C12N 15/00* (2006.01)
*C07H 21/04* (2006.01)

(52) U.S. Cl. ............... 435/134; 435/189; 435/252.3; 435/320.1; 536/23.2

(58) Field of Classification Search .......... 435/134, 435/189, 252.3, 320.1; 536/23.2
See application file for complete search history.

(56) References Cited

U.S. PATENT DOCUMENTS

| 5,968,809 | A | 10/1999 | Knutzon et al. |
| 7,067,285 | B2 | 6/2006 | Mukerji et al. |
| 7,335,476 | B2 | 2/2008 | Picataggio et al. |
| 2006/0117414 | A1 | 6/2006 | Qiu et al. |

FOREIGN PATENT DOCUMENTS

| WO | 02081668 A2 | 10/2002 |
| WO | 2004101753 A2 | 11/2004 |
| WO | 2007136671 A2 | 11/2007 |

OTHER PUBLICATIONS

International Search Report, PCT International Application No. PCT/US2009/52289, Mailed Oct. 14, 2009.
Z. Cohen et al., Fatty Acid Unsaturation in the Red Alga Porphyridium Cruentum. Is the Methylene Interrupted Nature of Polyunsatured Fatty Acids in an Intrinsic Property of the Desaturases?, Biochimica et Biophysica Acta, 1344 (1997) pp. 59-64.
I. Khozin et al., Elucidation of the Biosynthesis of Eicosapentaenoic Acid in the Microalga Porphyridium Cruentum, Plant Physiol., 114 (1997), pp. 223-230.
National Center for Biotechnology Information, *Phaeodactylum tricornutum* Delta-6 Desaturase, Genbank Accession No. AAL92563 (2002) pp. 1-3.
National Center for Biotechnology Information, *Mortierella isabellina* Delta-6 Desaturase, Genbank Accession No. AAL73948.1 (2002), pp. 1-3.
National Center for Biotechnology Information, *Mortierella alpina* Delta-6 Desaturase, Genbank Accession No. AAL73947 (2002), pp. 1-3.
National Center for Biotechnology Information, *Mortierella alpina* Delta-6 Desaturase, Genbank Accession No. AAF08685 (1999), pp. 1-3.
National Center for Biotechnology Information, *Marchantia polymorpha* Delta-6 Desaturase, Genbank Accession No. AAT85661 (2004), pp. 1-3.
National Center for Biotechnology Information, *Physcomitrella patens* Delta-6 Desaturase, Genbank Accession No. CAA11033 (2006), pp. 1-3.

*Primary Examiner* — Tekchand Saidha

(57) ABSTRACT

The present invention relates to Δ6 desaturases, which have the ability to convert linoleic acid ["LA"; 18:2 ω-6] to γ-linolenic acid ["GLA"; 18:3 ω-6] and/or α-linolenic acid ["ALA"; 18:3 ω-3] to stearidonic acid ["STA"; 18:4 ω-3]. Isolated nucleic acid fragments and recombinant constructs comprising such fragments encoding Δ6 desaturases, along with methods of making long-chain polyunsaturated fatty acids ["PUFAs"] using these Δ6 desaturases in oleaginous yeast, are disclosed.

12 Claims, 4 Drawing Sheets

FIG. 2

US 8,148,121 B2

Δ6 DESATURASES AND THEIR USE IN MAKING POLYUNSATURATED FATTY ACIDS

Figure 1A:
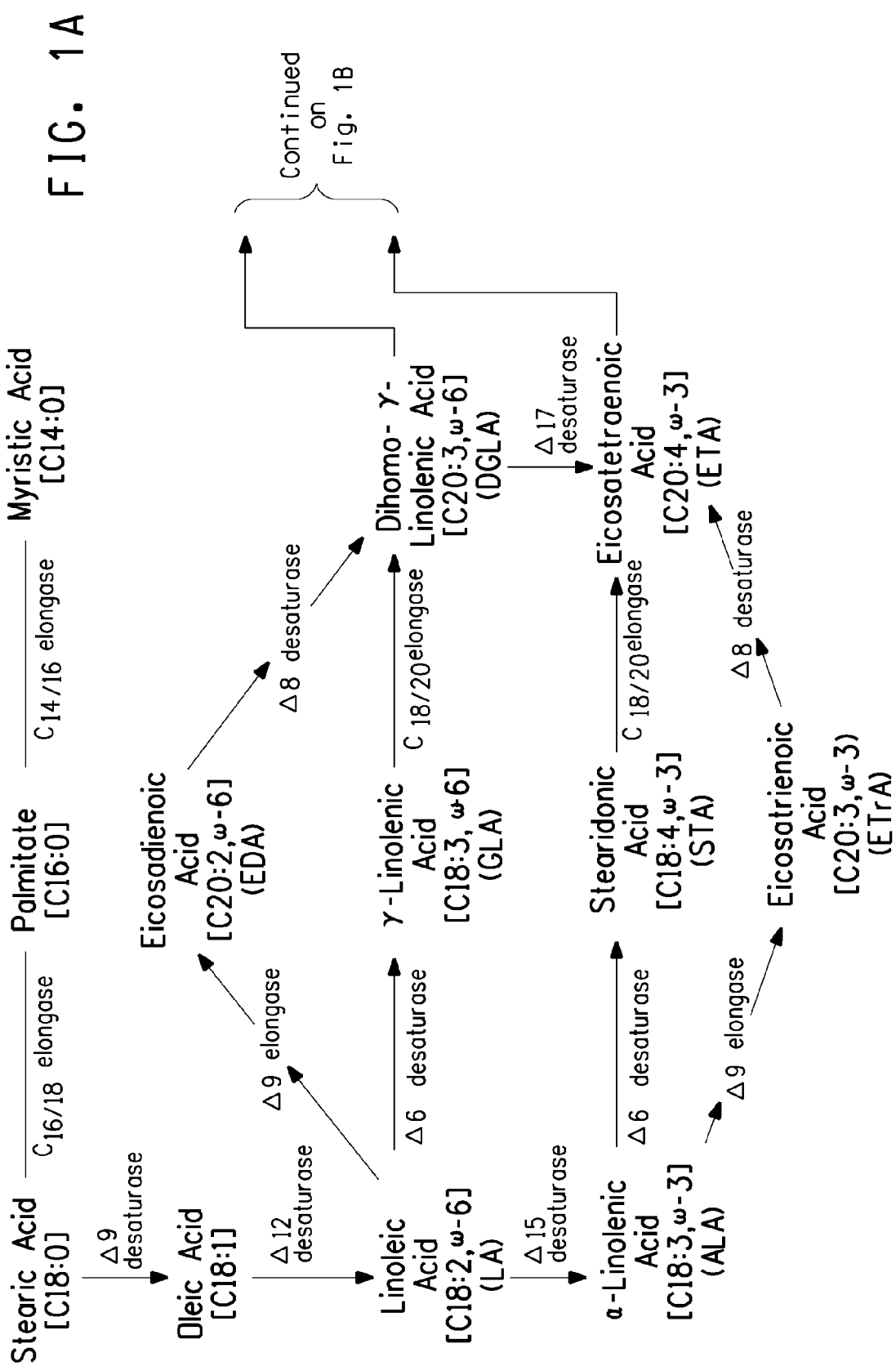

This application claims the benefit of U.S. Provisional Application No. 61/085,482, filed Aug. 1, 2008, the disclosure of which is hereby incorporated by reference in its entirety.

FIELD OF THE INVENTION

This invention is in the field of biotechnology. More specifically, this invention pertains to the identification of polynucleotide sequences encoding Δ6 fatty acid desaturases and the use of these desaturases in making long-chain polyunsaturated fatty acids ["PUFAs"].

BACKGROUND OF THE INVENTION

A variety of different hosts including plants, algae, fungi, stramenopiles and yeast are being investigated as means for commercial polyunsaturated fatty acid ["PUFA"] production. Genetic engineering has demonstrated that the natural abilities of some hosts (even those natively limited to linoleic acid [LA; 18:2 ω-6] and α-linolenic acid [ALA; 18:3 ω-3] fatty acid production) can be substantially altered to result in high-level production of various long-chain ω-3/ω-6 PUFAs. Whether this is the result of natural abilities or recombinant technology, production of arachidonic acid [ARA; 20:4 ω-6], eicosapentaenoic acid [EPA; 20:5 ω-3] and docosahexaenoic acid [DHA; 22:6 ω-3] may all require expression of a Δ6 desaturase.

Most Δ6 desaturase enzymes identified thus far have the primary ability to convert LA to γ-linolenic acid [GLA; 18:3 ω-6], with secondary activity in converting ALA to stearidonic acid [STA; 18:4 ω-3]. Based on the role Δ6 desaturase enzymes may play in the synthesis of e.g., ARA, EPA and DHA, there has been considerable effort to identify and characterize these enzymes from various sources. As such, numerous Δ6 desaturases have been disclosed in both the open literature (e.g., GenBank) and the patent literature (e.g., U.S. Pat. Nos. 5,968,809, 7,067,285, and 7,335,476 and U.S. Pat. Appl. Pub. No. 2006-0117414). Along with Δ5, Δ8 and Δ4 desaturases, Δ6 desaturases are known as long-chain PUFA "front-end" desaturases (wherein desaturation occurs between a pre-existing double bond and the carboxyl terminus of the fatty acid's acyl group, as opposed to methyl-directed desaturation). These desaturases are characterized by three histidine boxes [H(X)$_{3-4}$H (SEQ ID NOs:3 and 4), H(X)$_{2-3}$HH (SEQ ID NOs:5 and 6) and H/Q(X)$_{2-3}$HH (SEQ ID NOs:7 and 8)] and are members of the cytochrome b$_5$ fusion superfamily, since they possess a fused cytochrome b$_5$ domain at their N-terminus which serves as an electron donor.

Although genes encoding Δ6 desaturases are known, there is a need for additional varieties of these enzymes with varying enzymatic properties that are suitable for heterologous expression in a variety of host organisms for use in the production of ω-3/ω-6 fatty acids. Applicants have addressed the stated need by isolating genes encoding Δ6 desaturases from the red alga, *Porphyridium cruentum*.

SUMMARY OF THE INVENTION

The present invention relates to new genetic constructs encoding polypeptides having Δ6 desaturase activity, and their use in algae, bacteria, yeast, euglenoids, oomycetes, stramenopiles and fungi for the production of PUFAs.

Accordingly provided herein is an isolated nucleic acid molecule comprising a nucleotide sequence encoding a Δ6 desaturase enzyme, selected from the group consisting of:
  (a) an isolated nucleic acid molecule encoding the amino acid sequence as set forth in SEQ ID NO:2;
  (b) an isolated nucleic acid molecule that hybridizes with
    (a) under the following hybridization conditions: 0.1× SSC, 0.1% SDS, 65° C. and washed with 2×SSC, 0.1% SDS followed by 0.1×SSC, 0.1% SDS; or,
    an isolated nucleic acid molecule that is completely complementary to (a) or (b).

In a second embodiment, the invention provides an isolated nucleic acid molecule comprising a first nucleotide sequence encoding a Δ6 desaturase enzyme of at least 471 amino acids that has at least 80% identity based on the BLASTP method of alignment when compared to a polypeptide having the sequence as set forth in SEQ ID NO:2;
  or a second nucleotide sequence comprising the complement of the first nucleotide sequence.

In a third embodiment, the invention provides polypeptides encoded by the nucleic acid sequences of the invention and microbial host cells comprising the same.

In a forth embodiment, the invention provides a method for the production of γ-linolenic acid comprising:
  a) providing a microbial host cell expressing the nucleic acid sequence of claim 1 or claim 4; and
  b) growing the host cell of (a) in the presence of a source of linoleic acid under conditions wherein γ-linolenic acid is produced.

In a fifth embodiment, the invention provides a method for the production of stearidonic acid comprising:
  a) providing a microbial host cell expressing the nucleic acid sequence of either Claim 1 or claim 4; and
  b) growing the host cell of (a) in the presence of a source of α-linolenic acid under conditions wherein stearidonic acid is produced.

BRIEF DESCRIPTION OF THE DRAWINGS AND SEQUENCE LISTINGS

Figure 1B:
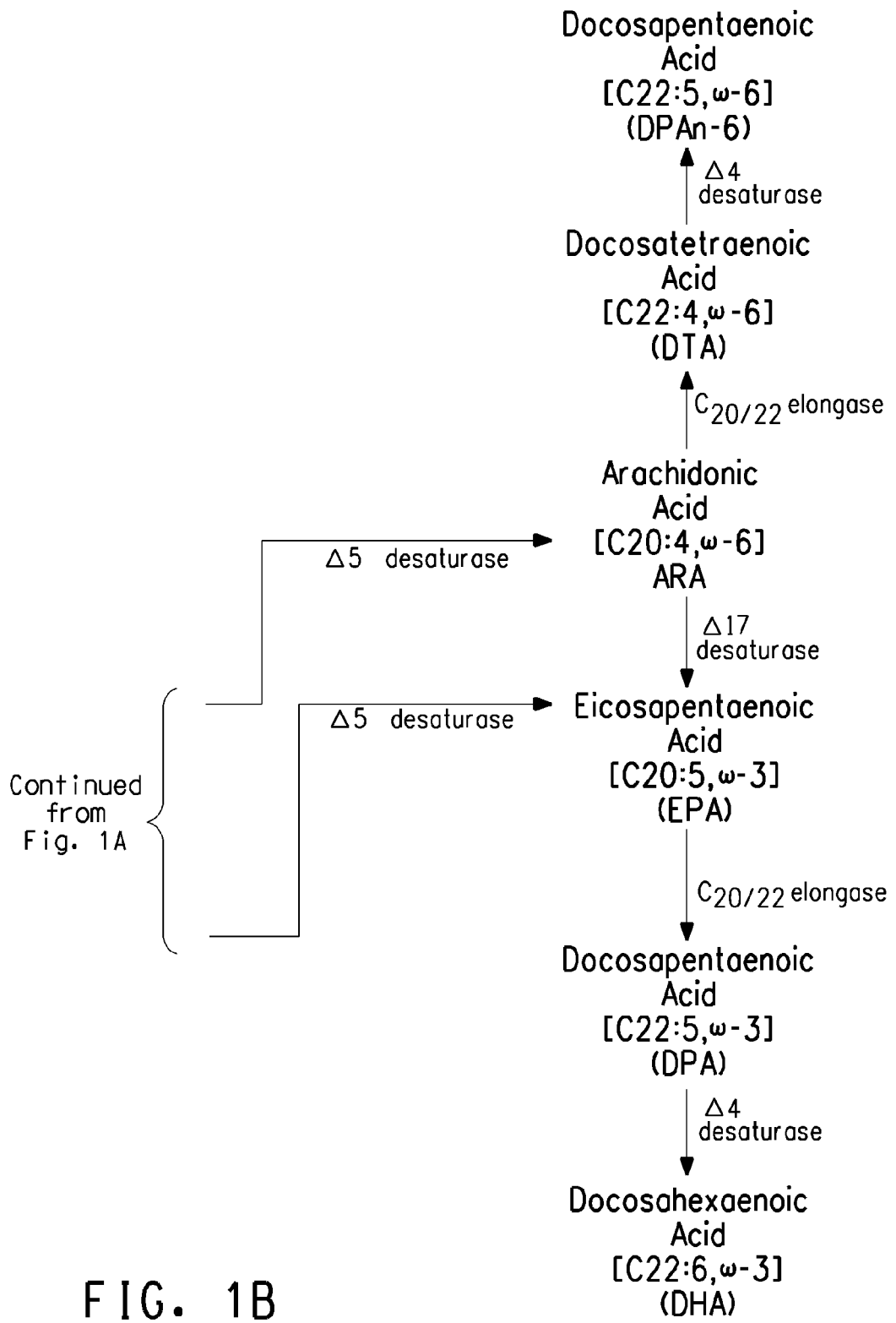

FIG. 1A and FIG. 1B illustrate the ω-3 and ω-6 fatty acid biosynthetic pathway, and should be viewed together when considering the description of this pathway below.

Figure 2:
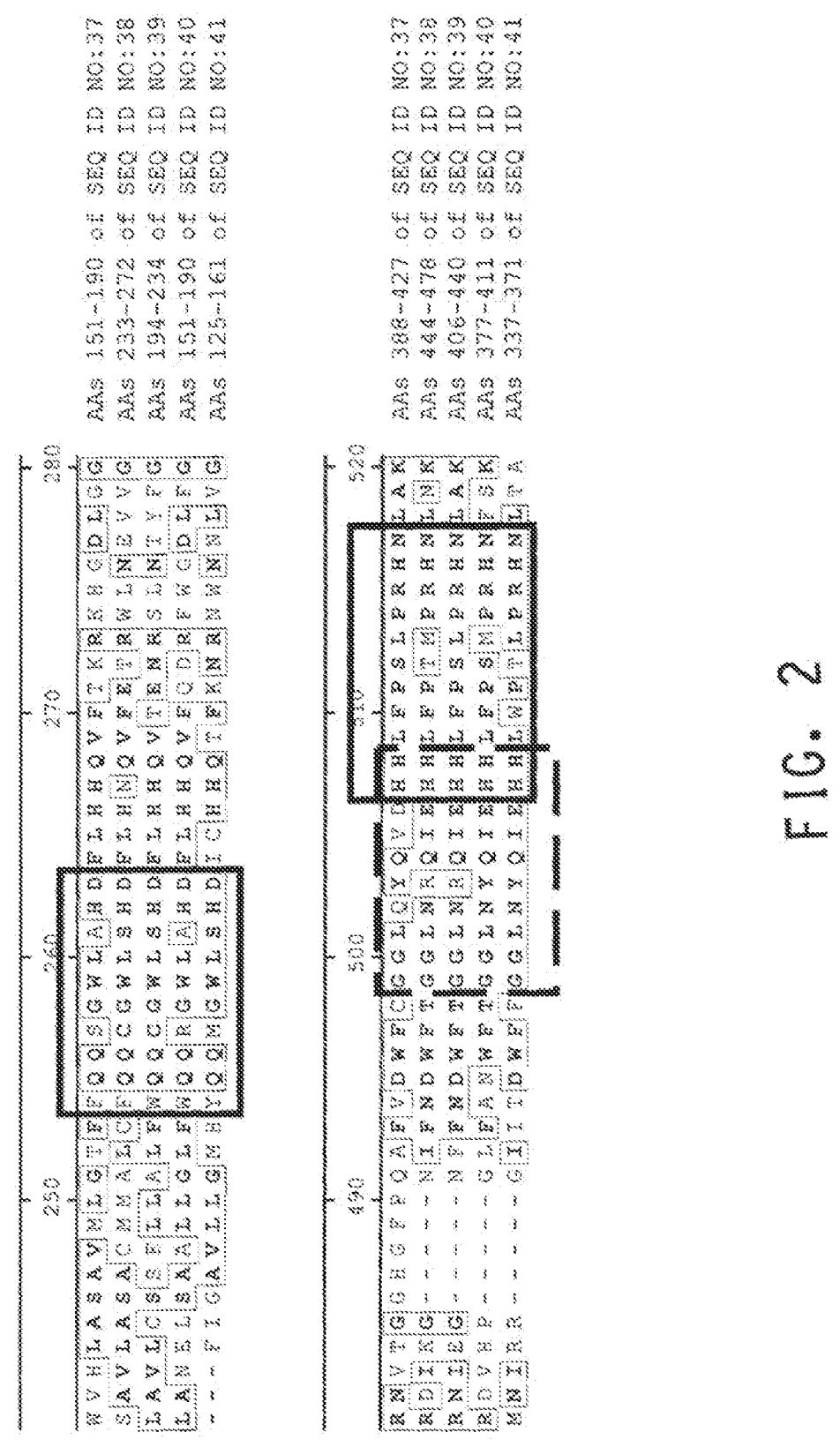

FIG. 2 is an alignment of two conserved regions in Δ6 desaturases from *Phaeodactylum tricornatum* (SEQ ID NO:37), *Physomitrella patens* (SEQ ID NO:38), *Marchantia polymnorpha* (SEQ ID NO:39), and *Mortierella alpina* (SEQ ID NO:40); and, the Δ8 desaturase from *Euglena gracilis* (SEQ ID NO:41) using the MegAlign™ v6.1 program of the LASERGENE bioinformatics computing suite (DNASTAR Inc., Madison, Wis.). The three boxed regions of conserved amino acids correspond to seven degenerate primers.

Figure 3:
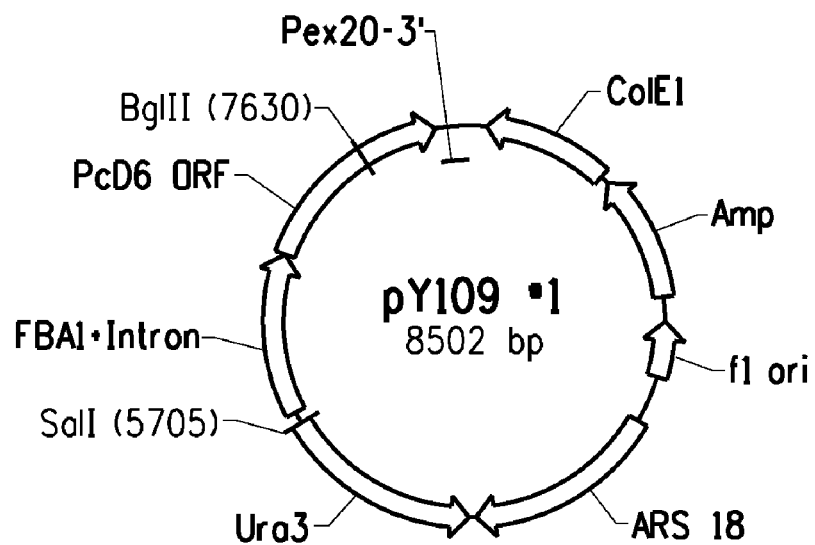

FIG. 3 is a plasmid map of pY109 #1.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-50 are ORFs encoding genes, proteins (or portions thereof), primers or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Porphyridium cruentum* Δ6 desaturase ["PcD6"] | 1 (1416 bp) | 2 (471 AA) |
| His-rich motif: H(X)$_3$H | — | 3 |
| His-rich motif: H(X)$_4$H | — | 4 |
| His-rich motif: H(X)$_2$HH | — | 5 |
| His-rich motif: H(X)$_3$HH | — | 6 |
| His-rich motif: H/Q(X)$_2$HH | — | 7 |
| His-rich motif: H/Q(X)$_3$HH | — | 8 |
| SMART IV oligonucleotide (from BD-Clontech Creator ™ Smart ™ cDNA library kit) | 9 | — |
| CDSIII/3' PCR primer (from BD-Clontech Creator ™ Smart ™ cDNA library kit) | 10 | — |
| 5'-PCR primer (from BD-Clontech Creator ™ Smart ™ cDNA library kit) | 11 | — |
| Primer 523 | 12 | — |
| Primer 524 | 13 | — |
| Primer 525 | 14 | — |
| Conserved amino acid sequence WQQMGWL(S/A)HD | — | 15 |
| Primer 526 | 16 | — |
| Primer 527 | 17 | — |
| Conserved amino acid sequence HHL(W/F)P(T/S)(M/L)PRH N | — | 18 |
| Primer 528 | 19 | — |
| Primer 529 | 20 | — |
| Conserved amino acid sequence GGL(N/H)YQIEHH | — | 21 |
| Primer T3 | 22 | — |
| Primer T7 | 23 | — |
| *Mortierella alpina* Δ6 desaturase (GenBank Accession No. AAF08685) | — | 24 (457 AA) |
| Primer 535 | 25 | — |
| Primer 536 | 26 | — |
| Primer 533 | 27 | — |
| Primer 534 | 28 | — |
| Primer 537 | 29 | — |
| Primer AUAP (from Invitrogen 5' RACE Kit) | 30 | — |
| Primer AAP (from Invitrogen 5' RACE Kit) | 31 | — |
| Primer 539 | 32 | — |
| Primer 540 | 33 | — |
| Plasmid pY91M | 34 (8423 bp) | — |
| Primer 373 | 35 | — |
| Primer 507 | 36 | — |
| *Phaeodactylum tricornutum* Δ6 desaturase (GenBank Accession No. AAL92563) | — | 37 (477 AA) |
| *Physcomitrella patens* Δ6 desaturase (GenBank Accession No. CAA11033) | — | 38 (525 AA) |
| *Marchantia polymorpha* Δ6 desaturase (GenBank Accession No. AAT85661) | — | 39 (481 AA) |
| *Mortierella alpina* Δ6 desaturase (GenBank Accession No. AAL73947) | — | 40 (457 AA) |
| *Euglena gracilis* Δ8 desaturase (GenBank Accession No. AAD45877) | — | 41 (419 AA) |
| *Porphyridium cruentum* Δ6 desaturase ["PcD6*"] | 42 (1416 bp) | 43 (471 AA) |
| Plasmid pY109 #1 | 44 (8502 bp) | — |
| Plasmid pY109 #2 | 45 (8502 bp) | — |
| Synthetic Δ6 desaturase, derived from *Porphyridium cruentum*, codon-optimized for expression in *Yarrowia lipolytica* ["PcD6S"] | 46 (1426 bp) | 47 (471 AA) |
| *Porphyridium cruentum* Δ6 desaturase His-rich motif HDFLH | — | 48 |
| *Porphyridium cruentum* Δ6 desaturase His-rich motif HNHHH | — | 49 |
| *Porphyridium cruentum* Δ6 desaturase His-rich motif QIEHH | — | 50 |
| *Porphyridium cruentum* Δ6 desaturase internal fragment | 51 (693 bp) | — |
| *Porphyridium cruentum* Δ6 desaturase 3' end fragment | 52 (410 bp) | — |
| *Porphyridium cruentum* Δ6 desaturase 5' end fragment | 53 (822 bp) | — |

DETAILED DESCRIPTION OF THE INVENTION

New *Porphyridium cruentum* Δ6 desaturase enzymes and genes encoding the same that may be used for the manipulation of biochemical pathways for the production of healthful PUFAs are disclosed herein.

PUFAs, or derivatives thereof, are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use, either human or veterinary.

All patent and non-patent literature cited herein is hereby incorporated by reference.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

"Total fatty acids" are abbreviated as "TFAs".

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and the chemical name of each compound.

TABLE 2

Nomenclature Of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | PA or Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Juniperonic | JUP | cis-5,11,14,17-eicosatetraenoic | 20:4b ω-3 |
| Eicosapentaenoic | EPA | cis-5,8,11,14,17-eicosapentaenoic | 20:5 ω-3 |
| Docosatrienoic | DRA | cis-10,13,16-docosatrienoic | 22:3 ω-6 |
| Docosatetraenoic | DTA | cis-7,10,13,16-docosatetraenoic | 22:4 ω-6 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Although the ω-3/ω-6 PUFAs listed in Table 3 are the most likely to be accumulated in the oil fractions of oleaginous yeast using the methods described herein, this list should not be construed as limiting or as complete.

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain long chain PUFAs and saturated fatty acids, as well as shorter chain saturated and unsaturated fatty acids.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the PC and the PE fractions) but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see U.S. Pat. Appl. Pub. No.2006-0115881-A1). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: $\Delta 4$ desaturase, $\Delta 5$ desaturase, $\Delta 6$ desaturase, $\Delta 12$ desaturase, $\Delta 15$ desaturase, $\Delta 17$ desaturase, $\Delta 9$ desaturase, $\Delta 8$ desaturase, $\Delta 9$ elongase, $C_{14/16}$ elongase, $C_{16/18}$ elongase, $C_{18/20}$ elongase and/or $C_{20/22}$ elongase.

The term "$\Delta 6$ desaturase/$\Delta 6$ elongase pathway" will refer to a PUFA biosynthetic pathway that minimally includes at least one $\Delta 6$ desaturase and at least one $C_{18/20}$ elongase (also referred to interchangeably as a $\Delta 6$ elongase), thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are $\Delta 6$ desaturases that desaturate a fatty acid between the sixth and seventh carbon atom numbered from the carboxyl-terminal end of the molecule and that can, for example, catalyze the conversion of LA to GLA and/or ALA to STA. Other fatty acid desaturases include, for example: Δ8 desaturases, Δ5 desaturases, Δ4 desaturases, Δ12 desaturases, Δ15 desaturases, Δ17 desaturases and Δ9 desaturases. In the art, Δ15 and Δ17 desaturases are also occasionally referred to as "omega-3 desaturases", "w-3 desaturases" and/or "ω-3 desaturases", based on their ability to convert ω-6 fatty acids into their ω-3 counterparts (e.g., conversion of LA into ALA and ARA into EPA, respectively). It may be desirable to empirically determine the specificity of a particular fatty acid desaturase by transforming a suitable host with the gene for the fatty acid desaturase and determining its effect on the fatty acid profile of the host.

For the purposes herein, the term "PcD6" refers to a Δ6 desaturase enzyme (SEQ ID NO:2) isolated from the red alga *Porphyridium cruentum*, encoded by the nucleotide sequence of SEQ ID NO:1 herein. Similarly, the term "PcD6S" refers to a synthetic Δ6 desaturase derived from *P. cruentum* that is codon-optimized for expression in *Yarrowia lipolytica* (i.e., SEQ ID NOs:46 and 47).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Pat. Appl. Pub. No. 2005/0132442. Examples of reactions catalyzed by elongase systems are the conversion of GLA to DGLA, STA to ETA, LA to EDA, ALA to ETrA, ARA to DTA and EPA to DPA.

In general, the substrate selectivity of elongases is somewhat broad but segregated by both chain length and the degree of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., LA, ALA, GLA, STA) and a $C_{20/22}$ elongase will utilize a $C_{20}$ substrate (e.g., ARA, EPA). For the purposes herein, two distinct types of $C_{18/20}$ elongases can be defined: a Δ6 elongase will catalyze conversion of GLA and STA to DGLA and ETA, respectively, while a Δ9 elongase is able to catalyze the conversion of LA and ALA to EDA and ETrA, respectively.

It is important to note that some elongases have broad specificity and thus a single enzyme may be capable of catalyzing several elongase reactions (e.g., thereby acting as both a $C_{16/18}$ elongase and a $C_{18/20}$ elongase). It may be desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of oil (Weete, In: Fungal Lipid Biochemistry, $2^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil.

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Motifs that are universally found in Δ6 desaturase enzymes (i.e., animal, plants and fungi) include three histidine boxes (i.e., $H(X)_{3-4}H$ (SEQ ID NOs:3 and 4), $H(X)_{2-3}HH$ (SEQ ID NOs:5 and 6) and $H/Q(X)_{2-3}HH$ (SEQ ID NOs:7 and 8)).

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability, corresponding to higher Tm, of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, e.g., 0.5× SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments, such as homologous sequences from distantly related organisms, to highly similar fragments, such as genes that duplicate functional enzymes from closely related organisms.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have at least about 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ["$T_m$"] for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; and, low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

The term "percent identity" refers to a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: N.J. (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: N.Y. (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191(1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information (NCBI) to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 50% to 100%, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. Accordingly, described herein is any nucleic acid fragment that encodes all or a substantial portion of the amino acid sequence encoding the algal polypeptide substantially as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequence" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in a sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into polypeptide. Thus, the term "expression", as used herein, also refers to the production of a functional end-product (e.g., an mRNA or a protein [either precursor or mature]).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for enhanced expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., $EMBO\ J.$, 4:2411-2418 (1985); De Almeida et al., $Mol.\ Gen.\ Genetics$, 218:78-86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., $J.\ Mol.\ Biol.$, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, $Comput.\ Methods\ Genome\ Res.$, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., $Experiments\ with\ Gene\ Fusions$, Cold Spring Harbor Laboratory: Cold Spring Harbor, N.Y. (1984); and by Ausubel, F. M. et al., $Current\ Protocols\ in\ Molecular\ Biology$, published by Greene Publishing Assoc. and Wiley-Interscience, Hoboken, N.J. (1987).

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238,482. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1) the esterification of one molecule of acyl-CoA to glycerol-3-phosphate via an acyltransferase to produce lysophosphatidic acid; 2) the esterification of a second molecule of acyl-CoA via an acyltransferase to yield 1,2-diacylglycerol phosphate (commonly identified as phosphatidic acid); 3) removal of a phosphate by phosphatidic acid phosphatase to yield 1,2-diacylglycerol ["DAG"]; and, 4) the addition of a third fatty acid by the action of an acyltransferase to form TAG. A wide spectrum of fatty acids can be incorporated into TAGs, including saturated and unsaturated fatty acids and short-chain and long-chain fatty acids.

The metabolic process wherein oleic acid is converted to $\omega$-3/$\omega$-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, multiple alternate pathways exist for production of a specific $\omega$-3/$\omega$-6 fatty acid.

Specifically, FIG. 1 depicts the pathways described below. All pathways require the initial conversion of oleic acid to linoleic acid ["LA"], the first of the $\omega$-6 fatty acids, by a $\Delta$12 desaturase. Then, using the "$\Delta$6 desaturase/$\Delta$6 elongase pathway" and LA as substrate, long chain $\omega$-6 fatty acids are formed as follows: 1) LA is converted to $\gamma$-linolenic acid ["GLA"] by a $\Delta$6 desaturase; 2) GLA is converted to dihomo-$\gamma$-linolenic acid ["DGLA"] by a $C_{18/20}$ elongase; 3) DGLA is converted to arachidonic acid ["ARA"] by a $\Delta$5 desaturase; 4) ARA is converted to docosatetraenoic acid ["DTA"] by a $C_{20/22}$ elongase; and, 5) DTA is converted to docosapentaenoic acid ["DPAn-6"] by a $\Delta$4 desaturase. Alternatively, the "$\Delta$6 desaturase/$\Delta$6 elongase" can use a-linolenic acid ["ALA"] as substrate to produce long chain $\omega$-3 fatty acids as follows: 1) LA is converted to ALA, the first of the $\omega$-3 fatty acids, by a $\Delta$15 desaturase; 2) ALA is converted to stearidonic acid ["STA"] by a $\Delta$6 desaturase; 3) STA is converted to eicosatetraenoic acid ["ETA"] by a $C_{18/20}$ elongase; 4) ETA is converted to eicosapentaenoic acid ["EPA"] by a $\Delta$5 desaturase; 5) EPA is converted to docosapentaenoic acid ["DPA"] by a $C_{20/22}$ elongase; and, 6) DPA is converted to docosahexaenoic acid ["DHA"] by a $\Delta$4 desaturase. Optionally, $\omega$-6 fatty acids may be converted to $\omega$-3 fatty acids; for example, ETA and EPA are produced from DGLA and ARA, respectively, by $\Delta$17 desaturase activity.

Alternate pathways for the biosynthesis of $\omega$-3/$\omega$-6 fatty acids utilize a $\Delta$9 elongase and $\Delta$8 desaturase (i.e., the "$\Delta$9 elongase/$\Delta$8 desaturase pathway"). More specifically, LA and ALA may be converted to eicosadienoic acid ["EDA"] and eicosatrienoic acid ["ETrA"], respectively, by a $\Delta$9 elongase; then, a Δ8 desaturase converts EDA to DGLA and/or ETrA to ETA. Downstream PUFAs are subsequently formed as described above.

It is contemplated that the particular functionalities required to be introduced into a specific host organism for production of ω-3/ω-6 fatty acids will depend on the host cell (and its native PUFA profile and/or desaturase/elongase profile), the availability of substrate, and the desired end product(s). For example, expression of the Δ6 desaturase/Δ6 elongase pathway may be preferred in some embodiments, as opposed to expression of the Δ9 elongase/Δ8 desaturase pathway, since PUFAs produced via the former pathway are not devoid of GLA and/or STA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1) the substrate specificity of the polypeptide; 2) whether the polypeptide or a component thereof is a rate-limiting enzyme; 3) whether the desaturase or elongase is essential for synthesis of a desired PUFA; 4) co-factors required by the polypeptide; and/or, 5) whether the polypeptide was modified after its production (e.g., by a kinase or a prenyltransferase). The expressed polypeptide preferably has parameters compatible with the biochemical environment of its location in the host cell (see U.S. Pat. No. 7,238,482 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

The present disclosure relates to nucleotide sequences encoding Δ6 desaturases, isolated from *Porphyridium cruentum* and summarized below in Table 3.

TABLE 3

Summary Of *Porphyridium cruentum* Δ6 Desaturases

| Abbreviation | Nucleotide SEQ ID NO | Amino Acid SEQ ID NO |
|---|---|---|
| PcD6 | 1 | 2 |
| PcD6S | 46 | 47 |

*Note:
SEQ ID NO: 47 is identical in sequence to SEQ ID NO: 2.

Thus described herein is an isolated polynucleotide comprising a first nucleotide sequence encoding a Δ6 desaturase enzyme of at least 471 amino acids that has at least 80% identity based on the BLASTP method of alignment when compared to a polypeptide having the sequence as set forth in SEQ ID NO:2; or a second nucleotide sequence comprising the complement of the first nucleotide sequence.

Comparison of the *P. cruentum* Δ6 desaturase nucleotide base and deduced amino acid sequences to public databases, using a BLAST algorithm (Altschul, S. F., et al., *Nucleic Acids Res.* 25:3389-3402 (1997) and *FEBS J.*, 272:5101-5109 (2005); provided by the National Center for Biotechnology Information ["NCBI"]), reveals that the most similar known sequences are about 40% identical to the amino acid sequence of the present Δ6 desaturase over a length of 471 amino acids.

More preferred amino acid fragments are at least about 70%-80% identical to the sequences herein, where those sequences that are at least 80%-90% identical are particularly suitable and those sequences that are about at least 90%-95% identical are most preferred. Similarly, preferred Δ6 desaturases encoding nucleic acid sequences corresponding to the instant ORF are those encoding active proteins and which are at least about 70%-80% identical to the nucleic acid sequences encoding the Δ6 desaturase reported herein, where those sequences that are at least about 80%-90% identical are particularly suitable and those sequences that are at least about 90%-95% identical are most preferred.

In alternate embodiments, the instant PcD6 sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins, preferably those expressed in the largest amount, and determining which codons are used with highest frequency. Then, the coding sequence for a polypeptide of interest having e.g., desaturase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Thus, PcD6 (SEQ ID NO:1) was codon-optimized for expression in *Yarrowia lipolytica*. This was possible based on previous determination of the *Y. lipolytica* codon usage profile, identification of those codons that were preferred, and determination of the consensus sequence around the 'ATG' initiation codon (see U.S. Pat. Nos. 7,238,482 and 7,125,672). The resultant synthetic gene is referred to as PcD6S (SEQ ID NO:46). The protein sequence encoded by the codon-optimized Δ6 desaturase gene (i.e., SEQ ID NO:47) is identical to that of the wildtype protein sequence (i.e., SEQ ID NO:2).

One skilled in the art would be able to use the teachings herein to create various other codon-optimized Δ6 desaturase proteins suitable for optimal expression in alternate hosts (i.e., other than *Yarrowia lipolytica*), based on the wildtype PcD6 sequence. Accordingly, the disclosure herein relates to any codon-optimized Δ6 desaturase protein that is derived from the wildtype sequence of PcD6 (i.e., encoded by SEQ ID NO:2). This includes, but is not limited to, the nucleotide sequence set forth in SEQ ID NO:46, which encodes a synthetic Δ6 desaturase protein (i.e., PcD6S) that was codon-optimized for expression in *Yarrowia lipolytica*. In alternate embodiments, it may be desirable to modify a portion of the codons encoding PcD6 to enhance expression of the gene in a host organism including, but not limited to, a plant or plant part, algae, bacteria, alternate yeast, euglenoid, oomycetes, stramenopiles or fungi.

Any of the instant desaturase sequences (i.e., PcD6 or PcD6S) or any portions thereof may be used to search for Δ6 desaturase homologs in the same or other bacterial, algal, fungal, oomycete, yeast, stramenopiles, euglenoid or plant species using sequence analysis software. In general, such computer software matches similar sequences by assigning degrees of homology to various substitutions, deletions, and other modifications.

Use of software algorithms, such as the BLASTP method of alignment with a low complexity filter and the following parameters: Expect value=10, matrix=Blosum 62 (Altschul, et al., *Nucleic Acids Res.* 25:3389-3402 (1997)), is well-known for comparing any Δ6 desaturase protein against a database of nucleic or protein sequences and thereby identifying similar known sequences within a preferred host organism.

Use of a software algorithm to comb through databases of known sequences is particularly suitable for the isolation of homologs having a relatively low percent identity to publicly available Δ6 desaturase sequences, such as those described in SEQ ID NO:2. It is predictable that isolation would be relatively easier for Δ6 desaturase homologs of at least about 70%-85% identity to publicly available desaturase sequences. Further, those sequences that are at least about 85%-90% identical would be particularly suitable for isolation and those sequences that are at least about 90%-95% identical would be the most facilely isolated.

Desaturase homologs can also be identified by the use of motifs unique to the desaturase enzymes. These motifs likely represent regions of the desaturase protein that are essential to the structure, stability or activity of the protein and these motifs are useful as diagnostic tools for the rapid identification of novel desaturase genes. Motifs that are universally found in Δ6 desaturase enzymes (i.e., animal, plants and fungi) include three histidine boxes (i.e., $H(X)_{3-4}H$ (SEQ ID NOs:3 and 4), $H(X)_{2-3}HH$ (SEQ ID NOs:5 and 6) and $H/Q(X)_{2-3}HH$ (SEQ ID NOs:7 and 8)). All three of these motifs are present in PcD6 (SEQ ID NO:2), providing further evidence that PcD6 is expected to have Δ6 desaturase activity.

Alternatively, any of the instant desaturase sequences or portions thereof may be hybridization reagents for the identification of Δ6 desaturase homologs. The basic components of a nucleic acid hybridization test include a probe, a sample suspected of containing the gene or gene fragment of interest and a specific hybridization method. Suitable probes are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added, such as guanidinium chloride, guanidinium thiocyanate, sodium thiocyanate, lithium tetrachloroacetate, sodium perchlorate, rubidium tetrachloroacetate, potassium iodide or cesium trifluoroacetate. If desired, one can add formamide to the hybridization mixture, typically 30-50% (v/v) ["by volume"].

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol ["weight by volume"] glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Any of the Δ6 desaturase nucleic acid fragments or any identified homologs may be used to isolate genes encoding homologous proteins from the same or other bacterial, algal, fungal, oomycete, yeast, stramenopiles, euglenoid or plant species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies such as polymerase chain reaction ["PCR"] (U.S. Pat. No. 4,683,202); ligase chain reaction ["LCR"] (Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

For example, genes encoding similar proteins or polypeptides to the Δ6 desaturases described herein could be isolated directly by using all or a portion of the nucleic acid fragments as DNA hybridization probes to screen libraries from any desired yeast or fungus using methodology well known to those skilled in the art (wherein those organisms producing GLA and/or STA would be preferred). Specific oligonucleotide probes based upon the nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the Δ6 desaturase sequences may be used in PCR protocols to amplify longer nucleic acid fragments encoding homologous genes from DNA or RNA. PCR may also be performed on a library of cloned nucleic acid fragments wherein the sequence of one primer is derived from the disclosed nucleic acid fragments. The sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl. Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the disclosed sequences. Using commercially available 3' RACE or 5' RACE systems (e.g., Gibco/BRL, Gaithersburg, Md.), specific 3' or 5' cDNA fragments can be isolated (Ohara et al., *Proc. Natl. Acad. Sci. U.S.A.*, 86:5673 (1989); Loh et al., *Science*, 243:217 (1989)).

Alternatively, any of the Δ6 desaturase nucleic acid fragments described herein (or any homologs identified thereof) may be used for creation of new and/or improved fatty acid desaturases. As is well known in the art, in vitro mutagenesis and selection, chemical mutagenesis, "gene shuffling" methods or other means can be employed to obtain mutations of naturally occurring desaturase genes (wherein such mutations may include deletions, insertions and point mutations, or combinations thereof). This would permit production of a polypeptide having desaturase activity, respectively, in vivo with more desirable physical and kinetic parameters for function in the host cell such as a longer half-life or a higher rate of production of a desired PUFA. Or, if desired, the regions of a polypeptide of interest (i.e., a Δ6 desaturase) important for enzymatic activity can be determined through routine mutagenesis, expression of the resulting mutant polypeptides and determination of their activities. An overview of these techniques is described in U.S. Pat. No. 7,238,482. All such mutant proteins and nucleotide sequences encoding them that are derived from PcD6 are within the scope of the present disclosure.

Improved fatty acids may also be synthesized by domain swapping, wherein a functional domain from any of the Δ6 desaturase nucleic acid fragments described herein is exchanged with a functional domain in an alternate desaturase gene to thereby result in a novel protein. As used herein, "domain" or "functional domain" refer to nucleic acid sequence(s) that are capable of eliciting a biological response in microbes.

Methods useful for manipulating biochemical pathways are well known to those skilled in the art. It is expected that introduction of chimeric genes encoding the Δ6 desaturases described herein (i.e., PcD6, PcD6S or other mutant enzymes, codon-optimized enzymes or homologs thereof), under the control of the appropriate promoters will result in increased production of GLA and/or STA in the transformed host organism, respectively. As such, disclosed herein are methods for the direct production of PUFAs comprising exposing a fatty acid substrate (i.e., LA and/or ALA) to the desaturase enzymes described herein (e.g., PcD6 or PcD6S), such that the substrate is converted to the desired fatty acid product (i.e., GLA and/or STA, respectively).

More specifically, provided herein is a method for the production of GLA in a microbial host cell (e.g., yeast, algae, bacteria, euglenoids, oomycetes, stramenopiles and fungi), wherein the microbial host cell comprises:
   a) a recombinant nucleotide molecule encoding a Δ6 desaturase polypeptide having at least 80% amino acid identity when compared to a polypeptide having the amino acid sequence as set forth in SEQ ID NO:2, based on the BLASTP method of alignment; and,
   b) a source of LA;
wherein the microbial host cell is grown under conditions such that the nucleic acid fragment encoding the Δ6 desaturase is expressed and the LA is converted to GLA, and wherein the GLA is optionally recovered.

In alternate embodiments, the Δ6 desaturase may be used for the conversion of ALA to STA. Accordingly provided herein is a method for the production of STA, wherein the microbial host cell comprises:
   a) a recombinant nucleotide molecule encoding a Δ6 desaturase polypeptide having at least 80% amino acid identity when compared to a polypeptide having the amino acid sequence as set forth in SEQ ID NO:2, based on the BLASTP method of alignment; and,
   b) a source of ALA;
wherein the microbial host cell is grown under conditions such that the nucleic acid fragment encoding the Δ6 desaturase is expressed and the ALA is converted to STA, and wherein the STA is optionally recovered.

Alternatively, each Δ6 desaturase gene and its corresponding enzyme product described herein can be used indirectly for the production of various ω-6 and ω-3 PUFAs (see FIG. 1 and U.S. Pat. No. 7,238,482). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ6 desaturases described herein (i.e., PcD6, PcD6S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ8 desaturases, Δ15 desaturases, Δ9 desaturases, Δ12 desaturases, $C_{14/16}$ elongases, $C_{16/18}$ elongases, Δ9 elongases, Δ5 desaturases, Δ4 desaturases, $C_{20/22}$ elongases) to result in higher levels of production of longer-chain ω-3/ω-6 fatty acids, such as e.g., ARA, EPA, DTA, DPAn-6, DPA and/or DHA.

In preferred embodiments, the disclosed Δ6 desaturases will minimally be expressed in conjunction with a $C_{18/20}$ elongase. However, the particular genes included within a particular expression cassette will depend on the host cell (and its PUFA profile and/or desaturase/elongase profile), the availability of substrate and the desired end product(s).

Alternately, it may be useful to disrupt a host organism's native Δ6 desaturase, based on the complete sequences described herein, the complement of those complete sequences, substantial portions of those sequences, codon-optimized desaturases derived therefrom and those sequences that are substantially homologous thereto.

It is necessary to create and introduce a recombinant construct comprising an open reading frame encoding a Δ6 desaturase (i.e., PcD6, PcD6S or other mutant enzymes, codon-optimized enzymes or homologs thereof) into a suitable host cell. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Sambrook, J., Fritsch, E. F. and Maniatis, T., Molecular Cloning: A Laboratory Manual, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from the genes native to the production host.

Transcription initiation control regions (also initiation control regions or promoters) useful for driving expression of the instant Δ6 desaturase ORFs in the desired microbial host cell are well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can be accomplished in an induced or constitutive fashion. Induced expression occurs by inducing the activity of a regulatable promoter operably linked to the gene of interest, while constitutive expression occurs by the use of a constitutive promoter.

When the host cell is yeast, transcriptional and translational regions functional in yeast cells are provided, particularly from the host species (e.g., see U.S. Pat. Appl. Pub. No. 2006-0115881-A1, corresponding to of Intl. App. Pub. No. WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts when utilized both in the same and different genera and species from where they were derived. Termination regions may also be derived from various genes native to the preferred hosts. The termination region is usually selected more for convenience rather than for any particular property. In alternate embodiments, the 3'-region can also be synthetic, as one of skill in the art can utilize available information to design and synthesize a 3'-region sequence that functions as a transcription terminator. A termination region may be unnecessary, but it is highly preferred.

Merely inserting a gene into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation and secretion from the microbial host cell. Some of the manipulated features include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the genome of the host cell; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these may be used in the methods and host cells described herein to further optimize expression of the Δ6 desaturases.

For example, Δ6 desaturase expression can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Alternately, additional copies of the Δ6 desaturase genes may be introduced into the recombinant host cells to thereby increase PUFA production and accumulation, either by cloning additional copies of genes within a single expression construct or by introducing additional copies into the host cell by increasing the plasmid copy number or by multiple integration of the cloned gene into the genome.

After a recombinant construct is created comprising at least one chimeric gene comprising a promoter, a Δ6 desaturase open reading frame ["ORF"] and a terminator, it is placed in a plasmid vector capable of autonomous replication in a host cell or is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell by any standard technique. These techniques include transformation, e.g., lithium acetate transformation (*Methods in Enzymology*, 194:186-187 (1991)), bolistic impact, electroporation, microinjection, vacuum filtration or any other method that introduces the gene(s) of interest into the host cell.

For convenience, a host cell that has been manipulated by any method to take up a DNA sequence, for example, in an expression cassette, is referred to herein as "transformed" or "transformant" or "recombinant". The transformed host will have at least one copy of the expression construct and may have two or more, depending upon whether the gene is integrated into the genome, amplified, or is present on an extra-chromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. Nos. 7,238,482, 7,259,255 and Intl. App. Pub. No. WO 2006/052870.

Following transformation, substrates suitable for the Δ6 desaturase (and, optionally other PUFA enzymes that are co-expressed within the host cell) may be produced by the host either naturally or transgenically, or they may be provided exogenously.

Regardless of the selected host or expression construct, multiple transformants must be screened to obtain a strain displaying the desired expression level and pattern. For example, Juretzek et al. (Yeast, 18:97-113 (2001)) note that the stability of an integrated DNA fragment in *Yarrowia lipolytica* is dependent on the individual transformants, the recipient strain and the targeting platform used. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western analysis of protein expression, phenotypic analysis or GC analysis of the PUFA products.

A variety of eukaryotic organisms are suitable as host, to thereby yield a transformant comprising Δ6 desaturases as described herein, including bacteria, yeast, algae, stramenopile, oomycete, euglenoid and/or fungus. This is contemplated because transcription, translation and the protein biosynthetic apparatus is highly conserved. Thus, suitable hosts may include those that grow on a variety of feedstocks, including simple or complex carbohydrates, fatty acids, organic acids, oils, glycerols and alcohols, and/or hydrocarbons over a wide range of temperature and pH values.

Preferred microbial hosts are oleaginous organisms. These oleaginous organisms are naturally capable of oil synthesis and accumulation, wherein the total oil content can comprise greater than about 25% of the dry cell weight, more preferably greater than about 30% of the dry cell weight, and most preferably greater than about 40% of the dry cell weight. Various bacteria, algae, euglenoids, moss, fungi, yeast and stramenopiles are naturally classified as oleaginous. In alternate embodiments, a non-oleaginous organism can be genetically modified to become oleaginous, e.g., yeast such as *Saccharomyces cerevisiae*.

In more preferred embodiments, the microbial host cells are oleaginous yeast. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis,* and *Yarrowia lipolytica* (formerly classified as *Candida lipolytica*). Most preferred is the oleaginous yeast *Yarrowia lipolytica;* and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) include U.S. Pat. Nos. 4,880,741 and 5,071,764 and Chen, D. C. et al. (*Appl. Microbiol. Biotechnol.*, 48(2):232-235 (1997)). Specific teachings applicable for engineering GLA, ARA, EPA and DHA production in *Y. lipolytica* are provided in U.S. patent application Ser. No. 11/198975 (Intl. App. Pub. No. WO 2006/033723), U.S. patent application Ser. No. 11/264784 (Intl. App. Pub. No. WO 2006/055322), U.S. patent application Ser. No. 11/265761 (Intl. App. Pub. No. WO 2006/052870) and U.S. patent application Ser. No. 11/264737 (Intl. App. Pub. No. WO 2006/052871), respectively.

The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No.

AJ001301), the Δ12 desaturase gene locus (U.S. Pat. No. 7,214,491), the Lip1 gene locus (GenBank Accession No. Z50020), the Lip2 gene locus (GenBank Accession No. AJ012632), the SCP2 gene locus (GenBank Accession No. AJ431362), the Pex3 gene locus (GenBank Accession No. CAG78565), the Pex16 gene locus (GenBank Accession No. CAG79622) and/or the Pex10 gene locus (GenBank Accession No. CAG81606)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants (U.S. Pat. Appl. Pub. No. 2009-0093543-A1), or a native acetohydroxyacid synthase (or acetolactate synthase; E.C. 4.1.3.18) that confers sulfonyl urea herbicide resistance (Intl. App. Pub. No. WO 2006/052870) is utilized for selection of transformants. A unique method of "recycling" a pair of preferred selection markers for their use in multiple sequential transformations, by use of site-specific recombinase systems, is also taught in U.S. Pat. Appl. Pub. No. 2009-0093543-A1.

Based on the above, disclosed herein is a method of producing either GLA or STA, respectively, comprising:
 (a) providing an oleaginous yeast (e.g., *Yarrowia lipolytica*) comprising:
  (i) a first recombinant nucleotide molecule encoding a Δ6 desaturase polypeptide, operably linked to at least one regulatory sequence; and,
  (ii) a source of desaturase substrate consisting of LA and/or ALA, respectively; and,
 (b) growing the yeast of step (a) in the presence of a suitable fermentable carbon source wherein the gene encoding the Δ6 desaturase polypeptide is expressed and LA is converted to GLA and/or ALA is converted to STA, respectively; and,
 (c) optionally recovering the GLA and/or STA, respectively, of step (b).

Substrate feeding may be required. In preferred embodiments, the Δ6 desaturase polypeptide is set forth as SEQ ID NO:2; thus, for example, the nucleotide sequence of the gene encoding the Δ6 desaturase polypeptide may be as set forth in SEQ ID NO:1 or SEQ ID NO:46 (wherein at least 227 codons have been optimized for expression in *Yarrowia* relative to SEQ ID NO:1).

Since naturally produced PUFAs in oleaginous yeast are limited to 18:2 fatty acids (i.e., LA), and less commonly, 18:3 fatty acids (i.e., ALA), the oleaginous yeast may be genetically engineered to express multiple enzymes necessary for long-chain PUFA biosynthesis (thereby enabling production of e.g., ARA, EPA, DPA and DHA), in addition to the Δ6 desaturases described herein.

Specifically, an oleaginous yeast is contemplated herein, wherein said yeast comprises:
 (a) a first recombinant DNA construct comprising an isolated polynucleotide encoding a Δ6 desaturase polypeptide, operably linked to at least one regulatory sequence; and,
 (b) at least one additional recombinant DNA construct comprising an isolated polynucleotide, operably linked to at least one regulatory sequence, encoding a polypeptide selected from the group consisting of: Δ4 desaturase, Δ5 desaturase, Δ9 desaturase, Δ12 desaturase, Δ15 desaturase, Δ17 desaturase, Δ8 desaturase, Δ9 elongase, $C_{14/16}$ elongase, $C_{16/18}$ elongase, $C_{18/20}$ elongase and $C_{20/22}$ elongase.

Other suitable microbial hosts include oleaginous bacteria, algae, euglenoids, stramenopiles, oomycetes and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ6 desaturase genes under the control of inducible or regulated promoters could yield a transformant organism capable of synthesizing increased quantities of GLA, which could be further converted to ARA by co-expression of a $C_{18/20}$ elongase and a Δ5 desaturase. The method of transformation of *M. alpina* is described by Mackenzie et al. (*Appl. Environ. Microbiol.*, 66:4655 (2000)). Similarly, methods for transformation of *Thraustochytriales* microorganisms (e.g., *Thraustochytrium*, *Schizochytrium*) are disclosed in U.S. Pat. No. 7,001,772.

Irrespective of the host selected for expression of the Δ6 desaturases described herein, multiple transformants must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Knowledge of the sequences of the present Δ6 desaturases will be useful for manipulating ω-3 and/or ω-6 fatty acid biosynthesis in various host cells. Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This manipulation may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art.

For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase GLA, ARA, EPA or DHA (and associated techniques thereof) are presented in Intl. App. Pub. No. WO 2006/033723, Intl. App. Pub. No. WO 2006/055322 [U.S. Pat. App. Pub. No. 2006-0094092-A1], Intl. App. Pub. No. WO 2006/052870 [U.S. Pat. App. Pub. No. 2006-0115881-A1] and Intl. App. Pub. No. WO 2006/052871 [U.S. Pat. App. Pub. No. 2006-0110806-A1], respectively, as are desirable manipulations in the TAG biosynthetic pathway and the TAG degradation pathway (and associated techniques thereof).

It may be useful to modulate the expression of the fatty acid biosynthetic pathway by any one of the strategies described above. For example, provided herein are methods whereby genes encoding key enzymes in the Δ6 desaturase/Δ6 elongase biosynthetic pathway are introduced into oleaginous yeasts for the production of ω-3 and/or ω-6 fatty acids. It will be particularly useful to express the present Δ6 desaturase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

The transformed microbial host cell is grown under conditions that optimize expression of chimeric genes (e.g., desaturase, elongase) and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in U.S. Pat. No. 7,238,482. Although it is contemplated that the source of carbon utilized in the methods herein may encompass a wide variety of carbon-containing sources, preferred carbon sources are sugars (e.g., glucose), glycerol, and/or fatty acids.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of PUFAs may include extraction (e.g., U.S. Pat. Nos. 6,797,303 and 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

There are a plethora of food and feed products incorporating ω-3 and/or ω-6 fatty acids, particularly e.g., ALA, GLA, ARA, EPA, DPA and DHA.

It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils containing ω-3 and/or ω-6 fatty acids will be suitable for use in a variety of food and feed products including, but not limited to: food analogs, meat products, cereal products, baked foods, snack foods and dairy products (see U.S. Pat. Appl. Pub. No. 2006-0094092 for details).

Additionally, the present compositions may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual;* Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* XL-2 cells (Catalog No. 200150) were purchased from Stratagene (San Diego, Calif.); *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" or "hr" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia Lipolytica*:

*Yarrowia lipolytica* strains with ATCC Accession Nos. #20362, #76982 and #90812 were purchased from the American Type Culture Collection (Rockville, Md.). *Yarrowia lipolytica* strains were typically grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco]; and 20 g of glucose.

Basic Minimal Media (MM) (per liter): 20 g glucose; 1.7 g yeast nitrogen base without amino acids; 1.0 g proline; and pH 6.1 (not adjusted).

Minimal Media+Tergitol (MMT) (per liter): Prepare MM media as above and add tergitol at 0.2% (wt/vol).

Minimal Media+5-Fluoroorotic Acid (MM+5-FOA) (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

Transformation of *Y. lipolytica* was performed as described in U.S. Pat. Appl. Pub. No. 2009-0093543-A1, hereby incorporated herein by reference.

Fatty Acid Analysis of *Yarrowia Lipolytica*:

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMES"] were prepared by transesterification of the lipid extract with sodium methoxide (Roughan, G. and Nishida I., *Arch Biochem Biophys.*, 276(1): 38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 μl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 μL hexane, the sample was vortexed and spun. The upper layer was removed and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (μg) of any fatty acid FAME ["μg FAME"] is calculated according to the formula: (area of the FAME peak for the specified fatty acid/area of the standard FAME peak) * (μg of the standard C15:0 TAG), while the amount (μg) of any fatty acid ["μg FA"] is calculated according to the formula: (area of the FAME peak for the specified fatty acid/area of the standard FAME peak) * (μg of the standard C15:0 TAG) * 0.9503, since 1 μg of C15:0 TAG is equal to 0.9503 μg fatty acids. Note that the 0.9503 conversion factor is an approximation of the value determined for most fatty acids, which range between 0.95 and 0.96.

The lipid profile, summarizing the amount of each individual fatty acid as a weight percent of TFAs, was determined by dividing the individual FAME peak area by the sum of all FAME peak areas and multiplying by 100.

Example 1

Construction of a *Porphyridium Cruentum* cDNA Library

The present Example describes the construction of a cDNA library of *Porphyridium cruentum* using the BD-Clontech Creator™ Smart™ cDNA library kit (Catalog No. K1053-1, Mississauga, ON, Canada), following preparation of total RNA and isolation of poly(A)+RNA.

Specifically, a culture of *P. cruentum* strain CCMP 1328 was purchased from The Provasoli-Guillard National Center for Culture of Marine Phytoplankton (Boothbay Harbor, Me.). Cells were pelleted by centrifugation at 3750 rpm in a Beckman GH3.8 rotor for 10 min and resuspended in 2×0.6 mL Trizole reagent (Invitrogen Corporation, Carlsbad, Calif.). Resuspended cells were transferred to two 2 mL screw cap tubes each containing 0.6 mL of 0.5 mm glass beads. The cells were homogenized at the HOMOGENIZE setting on a Biospec mini bead beater (Bartlesville, Okla.) for 2 min. The tubes were briefly spun to settle the beads. Liquid was transferred to 2 fresh 1.5 mL microfuge tubes and 0.2 mL chloroform/isoamyl alcohol (24:1) was added to each tube. The tubes were shaken by hand for 1 min and let stand for 3 min. The tubes were then spun at 14,000 rpm for 10 min at 4° C. The upper layer was transferred to 2 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol (made with RNase-free water) and air-dried. The total RNA sample was then redissolved in 500 μl of RNase free water.

Poly(A)+ RNA was isolated from the total RNA sample using a Qiagen oligoTex mRNA mini kit (Catalog No. 70022; Valencia, Calif.) according to the manufacturer's protocol. The total RNA sample was mixed with 500 μl of buffer OBB and 55 μl of Oligotex suspension. The mixture was incubated for 3 min at 70° C., and allowed to cool down at room temperature for 10 min. It was then centrifuged at 14,000 rpm in an Eppendorf microfuge for 2 min. The supernatant was discarded. The pellet was resuspended in 400 μl buffer OW2 and loaded onto a spin column supplied with the kit. The column was placed in a 1.5 mL microfuge tube and centrifuged at 14,000 rpm in an Eppendorf microfuge for 1 min. The column was transferred into a new 1.5 mL microfuge tube, and 400 µl of buffer OW2 was applied to the column. After centrifugation again at 14,000 rpm for 1 min, the column was transferred to a new RNase free 1.5 mL microfuge tube. Poly(A)+ RNA was eluted from the column by the addition of 20 µl buffer OEB preheated to 70° C., followed by centrifugation at 14,000 rpm for 1 min. The elution step was repeated once and the two eluted samples combined.

cDNA was generated using the LD-PCR method within the BD-Clontech Creator™ Smart™ cDNA library kit (formerly Catalog No. K1053-1; also designated as Catalog No. 634903) and 0.1 µg of polyA(+) RNA sample. Specifically, for 1$^{st}$ strand cDNA synthesis, 1 µl of the poly(A)+ RNA sample was mixed with 1 µl of SMART IV oligonucleotide (SEQ ID NO:9) and 1 µl of CDSIII/3' PCR primer (SEQ ID NO:10) in two 1.5 mL microfuge tubes. The mixtures were heated at 72° C. for 2 min and cooled on ice for 2 min. To each tube was added the following: 2 µl first strand buffer, 1 µl 20 mM DTT, 1 µl 10 mM dNTP mix and 1 µl Powerscript reverse transcriptase. The mixtures were incubated at 42° C. for 1 hr and cooled on ice.

The 1$^{st}$ strand cDNA synthesis mixture was used as template for the PCR reaction. Specifically, the reaction mixture contained the following: 2 µl of the 1$^{st}$ strand cDNA mixture, 2 µl 5'-PCR primer (SEQ ID NO:11), 2 µl CDSIII/3'-PCR primer (SEQ ID NO:10), 80 µl water, 10 µl 10× Advantage 2 PCR buffer, 2 µl 50× dNTP mix and 2 µl 50× Advantage 2 polymerase mix. Two reaction mixtures were set up. The thermocycler conditions were set for 95° C. for 20 sec, followed by 15 cycles of 95° C. for 5 sec and 68° C. for 6 min on a GenAmp 9600 instrument. PCR product was quantitated by agarose gel electrophoresis and ethidium bromide staining.

The PCR product was purified with a Qiagen PCR purification kit. For each reaction mixture, the PCR product was mixed with 500 µl of Buffer PB. The mixture was loaded into a spin column and centrifuged at 14,000 rpm for 1 min. The column was washed with 0.75 mL of buffer PE, and centrifuged at 14,000 rpm for 1 min. The column was then further centrifuged one more time at 14,000 rpm for 1 min. The cDNA sample was eluded by adding 50 µl of water to the column, allowing the column to sit at room temperature for 1 min, and centrifuging the column for 1 min at 14,000 rpm. The two samples were combined.

Purified cDNA was subsequently digested with SfiI (79 µl of the cDNA was mixed with 10 µl of 10× SfiI buffer, 10 µl of SfiI enzyme and 1 µl of 100× BSA and the mixture was incubated at 50° C. for 2 hrs). Xylene cyanol dye (2 µl of 1%) was added. The mixture was then fractionated on the Chroma Spin-400 column provided with the Creator™ Smart™ cDNA library kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 µl of water, and ligated into PDNR-LIB, supplied within the Creator™ Smart™ cDNA library kit.

Example 2

Cloning of a *Porphyridium Cruentum* Δ6 Desaturase

The fatty acid profile of the red alga, *Porphyridium cruentum* shows the presence of both EDA and GLA (Siran, D. et al., *Lipids*, 31(12):1277 (1996)), suggesting that biosynthesis of EPA in this alga may utilize either or both the Δ6 desaturase/Δ6 elongase pathway and/or the Δ9 elongase/Δ8 desaturase pathway. In an effort to clone a Δ8 desaturase from the organism, degenerate primers were used to isolate an internal portion of a desaturase-like protein.

Cloning and Sequencing of a PCR Product Encoding an Internal Portion of a *Porphyridium Cruentum* Desaturase-Like Protein An internal fragment of desaturase was cloned using degenerate PCR primers made against highly conserved amino acid regions in known Δ6 and Δ8 desaturases. For this, the Δ6 desaturases from *Phaeodactylum tricornatum* (GenBank Accession No. AAL92563 [gi_19879689]; SEQ ID NO:37), *Physomitrella patens* (GenBank Accession No. CAA11033 [gi_3790209]; SEQ ID NO:38), *Marchantia polymnorpha* (GenBank Accession No. AAT85661 [gi_50882491]; SEQ ID NO:39) and *Mortierella alpina* (GenBank Accession No. AAL73947 [gi_18483175]; SEQ ID NO:40) and the Δ8 desaturase from *Euglena gracilis* (GenBank Accession No. AAD45877 [gi_5639724]; SEQ ID NO:41) were aligned using the MegAlign™ v6.1 program of the LASERGENE bioinformatics computing suite (DNASTAR Inc., Madison, Wis.). Portions of this alignment are shown in FIG. 2; and, degenerate primers were designed to anneal to the boxed regions of conserved amino acid sequence shown in FIG. 2. Specifically, upper degenerate primers 523 (SEQ ID NO:12), 524 (SEQ ID NO:13) and 525 (SEQ ID NO:14) were made to the conserved amino acid sequence WQQMGWL(S/A)HD (SEQ ID NO:15). Lower degenerate primers 526 (SEQ ID NO:16) and 527 (SEQ ID NO:17) were made to the conserved amino acid sequence HHL(W/F)P(T/S)(M/L)PRHN (SEQ ID NO:18), while lower degenerate primers 528 (SEQ ID NO:19) and 529 (SEQ ID NO:20) were made to the conserved amino acid sequence GGL(N/H)YQIEHH (SEQ ID NO:21).

Four individual PCR reactions were performed using *Porphyridium cruentum* cDNA library (Example 1) as template and various combinations of the upper and lower degenerate primers, as described in Table 4.

TABLE 4

Degenerate PCR Reactions Performed To Isolate A Putative Desaturase

| PCR Reaction | Upper degenerate primer(s) | Lower degenerate primer(s) | Expected PCR product size |
|---|---|---|---|
| #1 | 523 and 524 (pooled) | 526 and 527 (pooled) | about 700 bp |
| #2 | 523 and 524 (pooled) | 528 and 529 (pooled) | about 700 bp |
| #3 | 525 | 526 and 527 (pooled) | about 700 bp |
| #4 | 525 | 528 and 529 (pooled) | about 700 bp |

PCR was performed using LA Taq™ DNA Polymerase (TaKaRa Bio Inc., Otsu, Shiga, 520-2193, Japan; Catalog No. TAK_RR002M) as per the manufacturer's instructions. The thermocycler conditions were 95° C. for 1 min, followed by 30 cycles of 95° C. for 1 min, 55° C. for 1 min, 72° C. for 1 min, followed by a final extension at 72° C. for 10 min. The PCR products were run in an agarose gel and the expected ~700 bp PCR fragments, which were observed in all reactions, were excised, purified using GeneClean kits (Qbiogene, Carlsbad, Calif.; Catalog No. 1001-600), and cloned into a pCR4-TOPO vector supplied in the TOPO TA cloning kit (Invitrogen Corporation, Carlsbad, Calif.; Catalog No. K4530-20). The ligation was transformed into *E. coli* XL-2 cells (Stratagene).

The cloned PCR products in plasmid DNA from six transformants were sequenced using T3 (SEQ ID NO:22) and T7

(SEQ ID NO:23) primers. The internal sequence, i.e., the sequence not including the degenerate upper and lower primer regions, of all six were similar to each other. More specifically, comparison of all 6 internal sequences revealed that they differed at a total of 17 different residues (of which only 5 were silent mutations). No two clones had identical variant residues suggesting that many of the variants were likely due to PCR error. The 693 bp sequence of one of the *Porphyridium cruentum* clones is shown as SEQ ID NO:51.

The identity of SEQ ID NO:51 was determined by conducting National Center for Biotechnology Information ["NCBI"] BLASTP 2.2.18 (protein-protein Basic Local Alignment Search Tool; Altschul et al., *Nucleic Acids Res.*, 25:3389-3402 (1997); and Altschul et al., *FEBS J.*, 272:5101-5109 (2005)) searches for similarity to sequences contained in the BLAST "nr" protein database using its translated sequence. The sequence was analyzed for similarity to all publicly available protein sequences contained in the "nr" database. The best hit (based on homology) to the cloned *P. cruentum* sequence was a *Mortierella alpina* Δ6 desaturase (Genbank Accession No. AAF08685.1; SEQ ID NO:24).

Cloning the 3' End of the Putative Desaturase

To clone the 3' end of the putative desaturase, the internal sequence of the PCR product cloned above was used to design forward gene specific PCR primers (i.e., primer 535 [SEQ ID NO:25] and primer 536 [SEQ ID NO:26]) for 3' nesting PCR.

Thus, PCR was performed as described above using the *Porphyridium cruentum* cDNA library from Example 1 as template and the primer pair comprising gene specific primer 535 (SEQ ID NO:25) and the CDSIII/3' PCR primer (SEQ ID NO:10; wherein the CDSIII/3' PCR primer having the sequence 5'-ATTCTAGAGGCCGAGGCGGCCGACATG-d(T)$_{30}$(A/G/C)N-3' was provided in the BD-Clontech Creator™ Smart™ cDNA library kit (Catalog No. K1053-1, Mississauga, ON, Canada)). The PCR reaction product was then subjected to a second, nested PCR reaction using the primer pair comprising gene specific primer 536 (SEQ ID NO:26) and the CDSIII/3' PCR primer (SEQ ID NO:10). The PCR reaction was run on a 1% agarose gel.

A PCR product of the predicted size (ca. 500 bp) was excised, purified using a GeneClean kit (Qbiogene), and ligated into a pCR4-TOPO vector supplied in the TOPO TA cloning kit (Invitrogen). Ligated DNA was transformed into *E. coli* XL-2 cells (Stratagene). The cloned PCR products were sequenced from plasmid DNA of 6 individual transformants. The 410 bp sequence from one clone is shown as SEQ ID NO:52.

Alignment of all sequences revealed variant nucleotide residues at 5 positions that were likely due to PCR error.

Cloning the 5' End of the Putative Desaturase

The 5' end of the putative desaturase cDNA was cloned using a 5' RACE Kit (Invitrogen Corporation, Carlsbad, Calif.; Catalog No. 18374-058), per the manufacturer's instructions. For this, the internal sequence of the PCR product cloned above was used to design reverse gene specific PCR primers (i.e., primer 533 [SEQ ID NO:27], primer 534 [SEQ ID NO:28] and primer 537 [SEQ ID NO:29]). The latter was designed to work with the AUAP primer (SEQ ID NO:30) in the 5' RACE kit.

The kit was used to synthesize first strand cDNA using gene specific primer 533 (SEQ ID NO:27) and *Porphyridium cruentum* total RNA (Example 1) as template. The first strand cDNA was treated with RNase, purified by S.N.A.P. column, and tailed with TdT as per the manufacturer's instructions.

The 5' end of the cDNA was amplified using the kit-provided forward AAP primer (SEQ ID NO:31), having the sequence 5'-GGCCACGCGTCGACTAGTACGGGI-IGGGIIGGGIIG-3', where I=deoxyinosine) and reverse gene specific primer 534 (SEQ ID NO:28) using the tailed cDNA as template. The PCR reaction was run on a 1% agarose gel.

Weak bands corresponding to the expected size (ca. 800 bp) were observed. All fragments between 500 and 1000 bp were excised, purified using a GeneClean kit (Qbiogene), and used as the template for a second nested 5' RACE using forward AUAP primer (SEQ ID NO:30) and reverse gene specific primer 537 (SEQ ID NO:29), as per the kit's instructions. The PCR reaction was run on a 1% agarose gel.

All PCR products were excised, purified using GeneClean kit (Qbiogene), and ligated into a pCR4-TOPO vector supplied in the TOPO TA cloning kit (Invitrogen). The ligation was transformed into *E. coli* XL-2 cells (Stratagene). The cloned PCR products were sequenced from plasmid DNA from 5 individual transformants. Alignment of the sequences revealed that 4 out of the 5 sequences were identical. This 822 bp sequence is shown as SEQ ID NO:53.

The fifth sequence had 3 mismatches (i.e., A441G, C653T and G722A, resulting in H125G and L196F mutations) relative to SEQ ID NO:53; however, this discrepancy in the sequence was again assumed to be likely due to PCR error.

The 5' end (SEQ ID NO:53), internal (SEQ ID NO:51) and 3' end (SEQ ID NO:52) sequences of the putative desaturase were assembled electronically to create a full-length DNA sequence (SEQ ID NO:1).

Cloning of the Full Length Desaturase cDNA

Since the 5' end, internal and 3' end sequences of the putative desaturase were obtained using LA Taq™ DNA Polymerase (TaKaRa Bio Inc.) that is not error-proof, the full length desaturase was cloned by PCR using the error proof PfuUltra™ High-Fidelity DNA Polymerase (Stratagene, San Diego, Calif.; Catalog No. 600380). For this, PCR was performed on *Porphyridium cruentum* cDNA library from Example 1 as template, using upper primer 539 (SEQ ID NO:32) and lower primer 540 (SEQ ID NO:33) that were designed based on the 5' and 3' end sequences of the putative desaturase clones above, as per the manufacturer's instructions. PCR product of the expected size (ca. 1470 bp) was excised and purified using a GeneClean kit (Qbiogene).

*Yarrowia* expression plasmid pY91 was derived from plasmid pY91M (SEQ ID NO:34; described in U.S. Pat. Appl. Pub. No. 2006-0115881-A1), following excision of the chimeric *Danio rerio* Δ6 desaturase ["DrD6"] gene by NcoI-NotI digestion. The 1470 bp PCR product comprising the full-length putative *Porphyridium cruentum* desaturase was then ligated between the NcoI and Not I sites of pY91 by in-fusion cloning (In-Fusion™ PCR Cloning kit, Catalog No. 631774; Clontech, Mountain View, Calif.), such that the cloned ORF was operably linked to the *Yarrowia lipolytica* FBAIN promoter (U.S. Pat. No. 7,202,356) and the Pex20 terminator sequence of the *Yarrowia* Pex20 gene (GenBank Accession No. AF054613).

Ligated DNA was transformed into *E. coli* XL-2 cells (Stratagene). Restriction analysis of plasmid DNA revealed that 6 out of 7 transformants had the expected Sal1/Bg/II fragments. The cloned cDNA ORF inserts in three of the these plasmids (i.e., mini prep #1, #2 and #4) were designated collectively as pY109. The ORFs were sequenced using upper and lower sequencing primers 373 (SEQ ID NO:35) and 507 (SEQ ID NO:36), respectively.

Alignment of the three cDNA sequences revealed that pY109 #1 and pY109 #4 were identical while pY109 #2 had 6 nucleotide residue differences, of which 5 resulted in amino acid substitutions. Variant residue A591T was a silent mutation, while variant residues C494T, T785C, T980C, C1052T and A1118G resulted in S165L, L262S, I327T, A351V and H373R amino acid variants (for each substitution listed [i.e. A591T], the first letter corresponds to the nucleotide or amino acid residue in pY109 #1 and the second letter corresponds to the nucleotide or amino acid residue found in the same position in pY109 #2, i.e. A591T indicates a change from adenine in pY109 #1 at position 591 to thymine in pY109 #2, while S165L indicates a change from serine in pY109 #1 at position 165 to leucine in pY109 #2). The H373R mutation is a highly conserved residue.

The 1416 nucleotide sequence of the *Porphyridium cruentum* Δ6 desaturase ORF (designated as "PcD6") in plasmid pY109#1 is shown in SEQ ID NO:1, while the deduced 471 amino acid sequence corresponding to SEQ ID NO:1 is shown as SEQ ID NO:2. Plasmid pY109 #1 (SEQ ID NO:44) is shown in FIG. 3, comprising the chimeric FBAIN::PcD6::Pex20 gene, as well as a ColE1 plasmid origin of replication, an ampicillin-resistance gene (Amp$^R$) for selection in *E. coli*, an *E. coli* f1 origin of replication, a *Yarrowia* autonomous replication sequence (ARS18; GenBank Accession No. A17608) and a *Yarrowia* Ura3 gene (GenBank Accession No. AJ306421).

The 1416 nucleotide sequence of the *Porphyridium cruentum* Δ6 desaturase ORF (designated as "PcD6*") in plasmid pY109 #2 is shown in SEQ ID NO:42, while the deduced 471 amino acid sequence corresponding to SEQ ID NO:42 is shown as SEQ ID NO:43. The nucleotide sequence of pY109 #2 is provided as SEQ ID NO:45.

The amino acid sequence of PcD6 (SEQ ID NO:2) was evaluated by NCBI's BLASTP 2.2.18 searches for similarity to sequences contained in the BLAST "nr" protein sequences database (comprising all non-redundant GenBank CDS translations, sequences derived from the 3-dimensional structure from Brookhaven Protein Data Bank (PDB), sequences included in the last major release of the SWISS-PROT protein sequence database, PIR and PRF excluding those environmental samples from WGS projects) using default parameters (expect threshold=10; word size=3; scoring parameters matrix=BLOSUM62; gap costs: existence=11, extension=1). The results of the BLASTP comparison summarizing the sequence to which SEQ ID NO:2 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, the results of BLASTP searches using the full length amino acid sequence of PcD6 (i.e., SEQ ID NO:2) as the query sequence showed that it shared 40% identity and 57% similarity with the Δ6 fatty acid desaturase of *Mortierella alpina* (GenBank Accession No. AAF08685.1), with an Expectation value of 5e-91. Additionally, PcD6 shared 39% identity and 57% similarity with the Δ6 desaturase of *Mortierella isabellina* (GenBank Accession No. AAL73948.1).

The three histidine boxes that are universally found in Δ6 desaturase enzymes (i.e., H(X)$_{3-4}$H (SEQ ID NOs:3 and 4), H(X)$_{2-3}$HH (SEQ ID NOs:5 and 6) and H/Q(X)$_{2-3}$HH (SEQ ID NOs:7 and 8)) were confirmed to be present in SEQ ID NO:2. Specifically, amino acids residues 198-202 of SEQ ID:2 are His-Asp-Phe-Leu-His [or HDFLH; SEQ ID NO:48]; amino acid residues 235-239 are His-Asn-His-His-His [or HNHHH; SEQ ID NO:49]; and, amino acid residues 416-420 are Gln-Ile-Glu-His-His [or QIEHH; SEQ ID NO:50].

Example 3

Functional Characterization of the Putative *Porphyridium Cruentum* Δ6 Desaturase ORFs Plasmids pY109 #1 (SEQ ID NO:44) and pY109 #2 (SEQ ID NO:45), each comprising a chimeric FBAIN::*Porphyridium cruentum* Δ6 desaturase::Pex20 gene, were transformed into various *Yarrowia lipolytica* strains. GC analysis demonstrated that PcD6 (SEQ ID NOs:1 and 2) in pY109 #1 could actively desaturate LA to GLA upon expression.

Isolation of *Yarrowia Lipolytica* Strains Y2224 And L103

Strain Y2224 (a FOA resistant mutant from an autonomous mutation of the Ura3 gene of wildtype *Yarrowia* strain ATCC #20362) was isolated as described in Example 13 of U.S. Pat. Appl. Pub. No. 2007-0292924-A1.

Strain L103, producing 47% ALA as a percent of total fatty acids ["TFAs"], was generated as described in Example 18 of U.S. Pat. Appl. Pub. No. 2006-0115881-A1. The genotype of this strain with respect to wildtype *Yarrowia lipolytica* ATCC #20362 was as follows: Ura3-, 3 copies of the chimeric FBAIN::FmD15:Lip2 gene (wherein FmD15 is a *Fusarium moniliforme* Δ15 desaturase gene; see also U.S. Pat. Appl. Pub. No. 2005-0132442-A1), 2 copies of the chimeric GPD::FmD15:XPR gene and 1 copy of the chimeric FBAIN::FmD12::Lip2 gene (wherein FmD12 is a *F. moniliforme* Δ12 desaturase gene; see also U.S. Pat. No. 7,504,259).

Transformation, Selection and Growth

Plasmid pY109 #1 and pY109 #2 (from Example 2, comprising PcD6 and PcD6*, respectively) were transformed into *Yarrowia lipolytica* strain Y2224 and *Yarrowia lipolytica* strain L103 by standard lithium acetate methods.

URA prototrophs were selected by growth on MM plates for three days. Four individual transformants of each strain were streaked onto fresh MM plates, incubated at 30° C. overnight, and used to inoculate 3 mL MM. Quadruplicate cultures of the Y2224 and L103 control strains were similarly prepared. After overnight growth in a 30° C. shaker, the cells were harvested and resuspended in MMT (MM+tergitol) containing a mixture of EDA and ETrA to a final fatty acid concentration of 0.5 mM each. Growth was continued for 24 hrs. Cells were harvested, washed with NP-40 (Catalog No.127087-87-0, Sigma, St. Louis, Mo.) and distilled water. Total lipids were extracted and transesterified. FAMEs were analyzed by GC, as described in the General Methods.

The fatty acid composition of 4 transformants of each strain is shown in the Table below, as well as the average fatty acid composition. Fatty acids are identified as 16:0, 18:0, 18:1 (ω-9), 18:2 (ω-6), GLA (18:3 ω-6), ALA (18:3 ω-3), STA (18:4 ω-3), EDA (20:2 ω-6), DGLA (20:3 ω-6), ARA (20:4 ω-6), ETrA (20:3 ω-3), ETA (20:4 ω-3) and EPA (20:5 ω-3). Conversion efficiency (abbreviated as "CE") is calculated as: ([product]/[substrate+product])*100. Thus, the "Δ6 CE" is calculated as: GLA/(LA+GLA)*100]; in contrast, the "Δ8 CE" is calculated as: DGLA/(EDA+DGLA)*100.

TABLE 5

Fatty Acid Composition (% Total Fatty Acid) In *Yarrowia lipolytica* Transformants

| Host | Plasmid | Transformant # | 16:0 | 16:1 n-11 | 18:0 | 18:1 n-9 | 18:2 n-6 | GLA 18:3 n-6 | ALA 18:3 n-3 | 17:1 | STA 18:4 n-3 |
|---|---|---|---|---|---|---|---|---|---|---|---|
| Y2224 | pY109 #1 | 1 | 16.5 | 13.4 | 4.5 | 47.0 | 9.6 | 3.3 | 0.0 | 0.7 | 0.0 |
|  |  | 2 | 15.9 | 12.7 | 4.5 | 48.1 | 9.6 | 3.0 | 0.0 | 0.7 | 0.0 |
|  |  | 3 | 17.0 | 12.9 | 4.9 | 47.3 | 9.4 | 3.3 | 0.0 | 0.6 | 0.0 |
|  |  | 4 | 17.0 | 13.2 | 4.8 | 47.4 | 9.1 | 3.1 | 0.0 | 0.7 | 0.0 |
|  |  | AVG | 16.6 | 13.0 | 4.7 | 47.4 | 9.4 | 3.1 | 0.0 | 0.7 | 0.0 |
| L103 | pY109 #2 | 5 | 11.8 | 7.5 | 4.6 | 31.6 | 14.5 | 0.0 | 24.1 | 0.4 | 0.0 |
|  |  | 6 | 12.0 | 7.8 | 4.0 | 26.5 | 15.2 | 0.0 | 28.0 | 0.4 | 0.0 |
|  |  | 7 | 12.0 | 7.7 | 4.2 | 30.9 | 15.3 | 0.0 | 24.4 | 0.3 | 0.0 |
|  |  | 8 | 12.0 | 7.5 | 4.3 | 29.5 | 16.4 | 0.0 | 24.1 | 0.4 | 0.0 |
|  |  | AVG | 12.0 | 7.6 | 4.3 | 29.6 | 15.3 | 0.0 | 25.1 | 0.4 | 0.0 |

| Host | Plasmid | Transformant # | EDA 20:2 n-6 | DGLA 20:3 n-6 | ARA 20:4 n-6 | ETrA 20:3 n-3 | ETA 20:4 n-3 | EPA 20:5 n-3 | Δ6 CE | Δ8 CE |
|---|---|---|---|---|---|---|---|---|---|---|
| Y2224 | pY109 #1 | 1 | 2.2 | 0.3 | 0.0 | 2.7 | 0.0 | 0.0 | 25.4 | 12.3 |
|  |  | 2 | 2.2 | 0.2 | 0.0 | 3.1 | 0.0 | 0.0 | 23.7 | 8.5 |
|  |  | 3 | 1.9 | 0.3 | 0.0 | 2.5 | 0.0 | 0.0 | 25.7 | 12.2 |
|  |  | 4 | 1.9 | 0.2 | 0.0 | 2.8 | 0.0 | 0.0 | 25.2 | 11.1 |
|  |  | AVG | 2.1 | 0.3 | 0.0 | 2.7 | 0.0 | 0.0 | 25.0 | 11.0 |
| L103 | pY109 #2 | 5 | 1.9 | 0.2 | 0.0 | 3.4 | 0.0 | 0.0 | 0.2 | 8.5 |
|  |  | 6 | 2.1 | 0.2 | 0.0 | 3.9 | 0.0 | 0.0 | 0.0 | 9.9 |
|  |  | 7 | 1.9 | 0.2 | 0.0 | 3.1 | 0.0 | 0.0 | 0.1 | 8.2 |
|  |  | 8 | 2.1 | 0.2 | 0.0 | 3.4 | 0.0 | 0.0 | 0.1 | 9.6 |
|  |  | AVG | 2.0 | 0.2 | 0.0 | 3.4 | 0.0 | 0.0 | 0.1 | 9.1 |

For comparison, the fatty acid composition (as a % of the TFAs) of wild type *Yarrowia lipolytica* strain ATCC #20362 grown at another time for 1 day in YPD, followed by 1 day in MMT is as follows: 7.9% of 16:0, 14.2% of 16:1 (n-11), 1.2% of 18:0, 50.0% of 18:1 (n-9) and 25.1% of 18:2 (n-6). GLA is absent in wild type ATCC #20362.

The presence of GLA in pY109 #1 transformants of *Yarrowia lipolytica* strain Y2224 is indicative of Δ6 desaturase activity encoded by the PcD6 ORF (SEQ ID NO:1) in Y109 #1. More specifically, the pY109 #1 (SEQ ID NO:44) transformants have 25% Δ6 desaturase conversion efficiency when expressed in *Y. lipolytica* strain Y2224. This conversion efficiency is expected to improve by codon optimization and chromosomal integration of the transgene.

In contrast, the absence of GLA in pY109 #2 transformants of *Y. lipolytica* strain L103 (a derivative of strain Y2224) is indicative of a lack of Δ6 desaturase activity encoded by the PcD6* ORF (SEQ ID NO:42) in Y109 #2 (SEQ ID NO:45). This is most likely attributable to the 5 amino acid residue differences in PcD6*, as compared to the PcD6 sequence expressed in pY109 #1.

The presence of trace amounts of DGLA in both pY109 #1 and pY109 #2 transformants suggests both have trace Δ8 desaturase activity. However, it is unclear if that is real or an artifact due to background levels of DGLA due to trace DGLA contamination in the exogenous fatty acid mixture.

In summary, this experimental data demonstrated that the *Porphyridium cruentum* Δ6 desaturase (i.e., PcD6, as set forth in SEQ ID NOs:1 and 2) actively desaturates LA to GLA when expressed in *Yarrowia lipolytica*.

Example 4

Synthesis of a Codon-Optimized Δ6 Desaturase Gene for *Yarrowia Lipolytica* (PcD6S)

The codon usage of the Δ6 desaturase gene ["PcD6"] of *Porphyridium cruentum* will be optimized for expression in *Yarrowia lipolytica*, in a manner similar to that described in Intl. App. Pub. No. WO 2004/101753 and U.S. Pat. No. 7,125,672. Specifically, a codon-optimized Δ6 desaturase gene (designated "PcD6S") will be designed based on the coding sequence of PcD6 (SEQ ID NO:1), according to the Yarrowia codon usage pattern (U.S. Pat. No. 7,125,672), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 248 bp of the 1416 bp coding region will be modified (17.5%) and 227 codons will be optimized (48.1%). A NcoI site and NotI site will be incorporated around the translation initiation codon and after the stop codon of PcD6S (SEQ ID NO:46), respectively. The protein sequence encoded by the codon-optimized gene will be identical to that of the wildtype protein sequence (i.e., SEQ ID NO:2). The designed PcD6S gene will be synthesized by GenScript Corporation (Piscataway, N.J.) and cloned into pUC57 (GenBank Accession No. Y14837) to generate pPcD6S.

One of skill in the art will be able to excise the PcD6S gene (SEQ ID NO:46) contained within pPcD6S, ligate it within a suitable expression vector comprising appropriate regulatory sequences (e.g., pY91, as set forth in SEQ ID NO:34), and express PcD6S in a suitable strain of *Yarrowia lipolytica*. It is expected that the Δ6 desaturase conversion efficiency of PcD6S will compare or exceed that of PcD6 (SEQ ID NOs:1 and 2).

What is claimed is:

1. An isolated nucleic acid molecule comprising a nucleotide sequence encoding a Δ6 desaturase enzyme, selected from the group consisting of:
   (a) an isolated nucleic acid molecule encoding the amino acid sequence as set forth in SEQ ID NO:2;
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or,
   an isolated nucleic acid molecule that is completely complementary to (a) or (b).

2. The isolated nucleic acid molecule of claim 1, wherein at least 227 codons are codon-optimized for expression in *Yarrowia*.

3. The isolated nucleic acid molecule of claim 1 selected from the group consisting of SEQ ID NO:1 and SEQ ID NO:46.

4. An isolated nucleic acid molecule comprising a first nucleotide sequence encoding a Δ6 desaturase enzyme of at least 471 amino acids that has at least 95% identity based on the BLASTP method of alignment when compared to a polypeptide having the sequence as set forth in SEQ ID NO:2; or a second nucleotide sequence comprising the complement of the first nucleotide sequence.

5. A chimeric gene comprising the isolated nucleic acid molecule of any one of claim 1 or 4 operably linked to at least one regulatory sequence.

6. A microbial host cell comprising the isolated nucleic acid sequence of claim 1 or claim 4.

7. The microbial host cell of claim 6 wherein the microbial host cell is selected from the group consisting of yeast, algae, bacteria, euglenoids, stramenopiles, oomycetes and fungi.

8. The microbial host cell of claim 7 wherein the cell is a member of a genus selected from the group consisting of *Mortierella, Thraustochytrium*, and *Schizochytrium*.

9. The microbial host cell of claim 7 wherein the cell is a yeast that is oleaginous.

10. The microbial host cell of claim 9 wherein the oleaginous yeast is member of a genus selected from the group consisting of: *Yarrowia, Candida, Rhodotorula, Rhodosporidium, Cryptococcus, Trichosporon* and *Lipomyces*.

11. A method for the production of γ-linolenic acid comprising:
   a) providing a microbial host cell of claim 6; and
   b) growing the host cell of (a) in the presence of a source of linoleic acid under conditions wherein γ-linolenic acid is produced.

12. A method for the production of stearidonic acid comprising:
   a) providing a microbial host cell of claim 6; and
   b) growing the host cell of (a) in the presence of a source of α-linolenic acid under conditions wherein stearidonic acid is produced.

* * * * *

SEQUENCE LISTING

<160> NUMBER OF SEQ ID NOS: 53

<210> SEQ ID NO 1
<211> LENGTH: 1416
<212> TYPE: DNA
<213> ORGANISM: Porphyridium cruentum
<220> FEATURE:
<221> NAME/KEY: CDS
<222> LOCATION: (1)..(1416)
<223> OTHER INFORMATION: delta-6 desaturase

<400> SEQUENCE: 1

| | | | | | | | | | | | | | | | | |
|---|---|---|---|---|---|---|---|---|---|---|---|---|---|---|---|---|
| atg | gcg | ccg | aat | gtg | gac | tcc | gga | agc | aag | gac | cgc | ggc | gtg | agc | gcg | 48 |
| Met | Ala | Pro | Asn | Val | Asp | Ser | Gly | Ser | Lys | Asp | Arg | Gly | Val | Ser | Ala | |
| 1 | | | | 5 | | | | | 10 | | | | | 15 | | |

| gtc | aaa | gaa | gta | gtc | tct | ggc | gcg | acg | gcc | aac | gcg | ctg | agt | ccg | gcc | 96 |
|---|---|---|---|---|---|---|---|---|---|---|---|---|---|---|---|---|
| Val | Lys | Glu | Val | Val | Ser | Gly | Ala | Thr | Ala | Asn | Ala | Leu | Ser | Pro | Ala | |
| | | 20 | | | | | 25 | | | | | 30 | | | | |

| gag | cgc | gtg | gtg | acc | agg | aag | gag | ctc | gcg | ggg | cac | gcc | tca | agg | gag | 144 |
|---|---|---|---|---|---|---|---|---|---|---|---|---|---|---|---|---|
| Glu | Arg | Val | Val | Thr | Arg | Lys | Glu | Leu | Ala | Gly | His | Ala | Ser | Arg | Glu | |
| | | | 35 | | | | | 40 | | | | | 45 | | | |

| tcg | gtg | tgg | att | gcg | gtg | aac | ggc | cgt | gtg | tac | gat | gtg | acc | ggc | ttt | 192 |
|---|---|---|---|---|---|---|---|---|---|---|---|---|---|---|---|---|
| Ser | Val | Trp | Ile | Ala | Val | Asn | Gly | Arg | Val | Tyr | Asp | Val | Thr | Gly | Phe | |
| | 50 | | | | | 55 | | | | | 60 | | | | | |

| gag | aac | gtt | cac | cct | ggc | ggc | gag | atc | att | ctg | acc | gcc | gcc | ggg | cag | 240 |
|---|---|---|---|---|---|---|---|---|---|---|---|---|---|---|---|---|
| Glu | Asn | Val | His | Pro | Gly | Gly | Glu | Ile | Ile | Leu | Thr | Ala | Ala | Gly | Gln | |
| 65 | | | | | 70 | | | | | 75 | | | | | 80 | |

| gac | gca | acg | gac | gtg | ttt | gcc | gcg | ttt | cac | acg | ccc | gcc | acg | tgg | aaa | 288 |
|---|---|---|---|---|---|---|---|---|---|---|---|---|---|---|---|---|
| Asp | Ala | Thr | Asp | Val | Phe | Ala | Ala | Phe | His | Thr | Pro | Ala | Thr | Trp | Lys | |
| | | | 85 | | | | | 90 | | | | | 95 | | | |

| atg | atg | ccg | cag | ttc | ctc | gtg | gga | aac | ctc | gag | gag | gac | gcg | ctc | tct | 336 |
|---|---|---|---|---|---|---|---|---|---|---|---|---|---|---|---|---|
| Met | Met | Pro | Gln | Phe | Leu | Val | Gly | Asn | Leu | Glu | Glu | Asp | Ala | Leu | Ser | |
| | | | 100 | | | | | 105 | | | | | 110 | | | |

| gcc | aaa | ccg | tct | aag | cag | ctt | aat | ggg | cat | tcg | cca | cac | gag | tac | caa | 384 |
|---|---|---|---|---|---|---|---|---|---|---|---|---|---|---|---|---|
| Ala | Lys | Pro | Ser | Lys | Gln | Leu | Asn | Gly | His | Ser | Pro | His | Glu | Tyr | Gln | |
| | | 115 | | | | | 120 | | | | | 125 | | | | |

| gct | gat | atc | cga | aag | atg | cgt | gcg | gaa | ctt | gtc | aag | ctg | cgc | gcg | ttc | 432 |
|---|---|---|---|---|---|---|---|---|---|---|---|---|---|---|---|---|
| Ala | Asp | Ile | Arg | Lys | Met | Arg | Ala | Glu | Leu | Val | Lys | Leu | Arg | Ala | Phe | |
| | 130 | | | | | 135 | | | | | 140 | | | | | |

| gac | tcg | aac | aag | ttc | ttc | tac | ctg | ttc | aag | ttc | ctg | tcc | acg | tct | gcg | 480 |
|---|---|---|---|---|---|---|---|---|---|---|---|---|---|---|---|---|
| Asp | Ser | Asn | Lys | Phe | Phe | Tyr | Leu | Phe | Lys | Phe | Leu | Ser | Thr | Ser | Ala | |
| 145 | | | | | 150 | | | | | 155 | | | | | 160 | |

| att | tgc | gcc | ctc | tcg | gtg | gtc | atg | gcg | ctc | ggc | atg | aag | gac | tcg | atg | 528 |
|---|---|---|---|---|---|---|---|---|---|---|---|---|---|---|---|---|
| Ile | Cys | Ala | Leu | Ser | Val | Val | Met | Ala | Leu | Gly | Met | Lys | Asp | Ser | Met | |
| | | | 165 | | | | | 170 | | | | | 175 | | | |

| atc | gtc | acg | gcg | ctc | gcc | gcg | ttc | acc | atg | gca | ctc | ttc | tgg | cag | cag | 576 |
|---|---|---|---|---|---|---|---|---|---|---|---|---|---|---|---|---|
| Ile | Val | Thr | Ala | Leu | Ala | Ala | Phe | Thr | Met | Ala | Leu | Phe | Trp | Gln | Gln | |
| | | | 180 | | | | | 185 | | | | | 190 | | | |

| tgc | ggc | tgg | ctc | gca | cac | gac | ttt | ctg | cac | cat | cag | gtg | ttc | aag | aac | 624 |
|---|---|---|---|---|---|---|---|---|---|---|---|---|---|---|---|---|
| Cys | Gly | Trp | Leu | Ala | His | Asp | Phe | Leu | His | His | Gln | Val | Phe | Lys | Asn | |
| | | 195 | | | | | 200 | | | | | 205 | | | | |

| agg | gtg | ttc | aac | aac | ctg | gtc | ggt | ctt | gtt | gtt | ggt | aat | gtc | tat | cag | 672 |
|---|---|---|---|---|---|---|---|---|---|---|---|---|---|---|---|---|
| Arg | Val | Phe | Asn | Asn | Leu | Val | Gly | Leu | Val | Val | Gly | Asn | Val | Tyr | Gln | |
| | 210 | | | | | 215 | | | | | 220 | | | | | |

| ggc | ttt | tcg | gta | tcc | tgg | tgg | aag | atg | aag | cac | aac | cac | cac | cac | gcc | 720 |
|---|---|---|---|---|---|---|---|---|---|---|---|---|---|---|---|---|
| Gly | Phe | Ser | Val | Ser | Trp | Trp | Lys | Met | Lys | His | Asn | His | His | His | Ala | |
| 225 | | | | | 230 | | | | | 235 | | | | | 240 | |

| gct | cca | aac | gtg | acg | tca | acg | gcc | gct | ggg | cca | gac | cca | gac | atc | gac | 768 |
|---|---|---|---|---|---|---|---|---|---|---|---|---|---|---|---|---|
| Ala | Pro | Asn | Val | Thr | Ser | Thr | Ala | Ala | Gly | Pro | Asp | Pro | Asp | Ile | Asp | |
| | | | 245 | | | | | 250 | | | | | 255 | | | |

```
act gtg ccc gtg ctc ttg tgg agc gag aaa ctc atc gag ggt gat agc        816
Thr Val Pro Val Leu Leu Trp Ser Glu Lys Leu Ile Glu Gly Asp Ser
        260                 265                 270 aag gag atg gag gat ctg ccc atg ttc ctc atg aag aac cag aag atc        864
Lys Glu Met Glu Asp Leu Pro Met Phe Leu Met Lys Asn Gln Lys Ile
    275                 280                 285 ttt tac tgg ccg gtt ctg tgc gtg gcg cgc atc agc tgg ctc ctg cag        912
Phe Tyr Trp Pro Val Leu Cys Val Ala Arg Ile Ser Trp Leu Leu Gln
290                 295                 300 agc ctt ctc ttc cag cgc gcg ccg gtc tgg aac ttt gtg ggc gga aac        960
Ser Leu Leu Phe Gln Arg Ala Pro Val Trp Asn Phe Val Gly Gly Asn
305                 310                 315                 320 agc tgg cgc gcg gtg gag atc gtc gcg ctt ctc atg cat cac ggc gcc       1008
Ser Trp Arg Ala Val Glu Ile Val Ala Leu Leu Met His His Gly Ala
            325                 330                 335 tac ttc tac ttg ctg tcc ttg ctc aag agc tgg gtc cat gtc gcg ctc       1056
Tyr Phe Tyr Leu Leu Ser Leu Leu Lys Ser Trp Val His Val Ala Leu
        340                 345                 350 ttt ttg gtg gtg agc cag gcg atg ggt ggt gtg cta ctc ggc gtc gtg       1104
Phe Leu Val Val Ser Gln Ala Met Gly Gly Val Leu Leu Gly Val Val
    355                 360                 365 ttc acc gtc ggg cac aac gcg atg aaa gtc ctc tcc gag gaa gaa atg       1152
Phe Thr Val Gly His Asn Ala Met Lys Val Leu Ser Glu Glu Glu Met
370                 375                 380 aag tca acc gac ttt gtc cag atg cag gtc ctg acg acg aga aat att       1200
Lys Ser Thr Asp Phe Val Gln Met Gln Val Leu Thr Thr Arg Asn Ile
385                 390                 395                 400 gag ccg acg gct ttc aat cgg tgg ttc agc ggt ggc ctc agc tac cag       1248
Glu Pro Thr Ala Phe Asn Arg Trp Phe Ser Gly Gly Leu Ser Tyr Gln
            405                 410                 415 att gag cac cac atc tgg cct cag ctg ccc cga cac agc tta ccc aag       1296
Ile Glu His His Ile Trp Pro Gln Leu Pro Arg His Ser Leu Pro Lys
        420                 425                 430 gcg cgc gaa att ctc acc aag ttt tgc agc aag tat gat att ccg tac       1344
Ala Arg Glu Ile Leu Thr Lys Phe Cys Ser Lys Tyr Asp Ile Pro Tyr
    435                 440                 445 gcc agt caa ggc ctc att gaa ggt aac atg gaa gtg tgg aaa atg ctc       1392
Ala Ser Gln Gly Leu Ile Glu Gly Asn Met Glu Val Trp Lys Met Leu
450                 455                 460 tcg aag ctt ggg gaa tcc cta tag                                        1416
Ser Lys Leu Gly Glu Ser Leu
465                 470

<210> SEQ ID NO 2
<211> LENGTH: 471
<212> TYPE: PRT
<213> ORGANISM: Porphyridium cruentum

<400> SEQUENCE: 2

Met Ala Pro Asn Val Asp Ser Gly Ser Lys Asp Arg Gly Val Ser Ala
1               5                   10                  15

Val Lys Glu Val Val Ser Gly Ala Thr Ala Asn Ala Leu Ser Pro Ala
            20                  25                  30

Glu Arg Val Val Thr Arg Lys Glu Leu Ala Gly His Ala Ser Arg Glu
        35                  40                  45

Ser Val Trp Ile Ala Val Asn Gly Arg Val Tyr Asp Val Thr Gly Phe
    50                  55                  60

Glu Asn Val His Pro Gly Gly Glu Ile Ile Leu Thr Ala Ala Gly Gln
65                  70                  75                  80

Asp Ala Thr Asp Val Phe Ala Ala Phe His Thr Pro Ala Thr Trp Lys
```

```
                        85                  90                  95
Met Met Pro Gln Phe Leu Val Gly Asn Leu Glu Glu Asp Ala Leu Ser
            100                 105                 110

Ala Lys Pro Ser Lys Gln Leu Asn Gly His Ser Pro His Glu Tyr Gln
            115                 120                 125

Ala Asp Ile Arg Lys Met Arg Ala Glu Leu Val Lys Leu Arg Ala Phe
            130                 135                 140

Asp Ser Asn Lys Phe Phe Tyr Leu Phe Lys Phe Leu Ser Thr Ser Ala
145                 150                 155                 160

Ile Cys Ala Leu Ser Val Val Met Ala Leu Gly Met Lys Asp Ser Met
                    165                 170                 175

Ile Val Thr Ala Leu Ala Ala Phe Thr Met Ala Leu Phe Trp Gln Gln
                    180                 185                 190

Cys Gly Trp Leu Ala His Asp Phe Leu His Gln Val Phe Lys Asn
                    195                 200                 205

Arg Val Phe Asn Asn Leu Val Gly Leu Val Val Gly Asn Val Tyr Gln
            210                 215                 220

Gly Phe Ser Val Ser Trp Trp Lys Met Lys His Asn His His His Ala
225                 230                 235                 240

Ala Pro Asn Val Thr Ser Thr Ala Ala Gly Pro Asp Pro Asp Ile Asp
                    245                 250                 255

Thr Val Pro Val Leu Leu Trp Ser Glu Lys Leu Ile Glu Gly Asp Ser
                    260                 265                 270

Lys Glu Met Glu Asp Leu Pro Met Phe Leu Met Lys Asn Gln Lys Ile
            275                 280                 285

Phe Tyr Trp Pro Val Leu Cys Val Ala Arg Ile Ser Trp Leu Leu Gln
            290                 295                 300

Ser Leu Leu Phe Gln Arg Ala Pro Val Trp Asn Phe Val Gly Gly Asn
305                 310                 315                 320

Ser Trp Arg Ala Val Glu Ile Val Ala Leu Leu Met His His Gly Ala
                    325                 330                 335

Tyr Phe Tyr Leu Leu Ser Leu Leu Lys Ser Trp Val His Val Ala Leu
                    340                 345                 350

Phe Leu Val Val Ser Gln Ala Met Gly Gly Val Leu Leu Gly Val Val
                    355                 360                 365

Phe Thr Val Gly His Asn Ala Met Lys Val Leu Ser Glu Glu Met
            370                 375                 380

Lys Ser Thr Asp Phe Val Gln Met Gln Val Leu Thr Thr Arg Asn Ile
385                 390                 395                 400

Glu Pro Thr Ala Phe Asn Arg Trp Phe Ser Gly Gly Leu Ser Tyr Gln
                    405                 410                 415

Ile Glu His His Ile Trp Pro Gln Leu Pro Arg His Ser Leu Pro Lys
            420                 425                 430

Ala Arg Glu Ile Leu Thr Lys Phe Cys Ser Lys Tyr Asp Ile Pro Tyr
            435                 440                 445

Ala Ser Gln Gly Leu Ile Glu Gly Asn Met Glu Val Trp Lys Met Leu
            450                 455                 460

Ser Lys Leu Gly Glu Ser Leu
465                 470

<210> SEQ ID NO 3
<211> LENGTH: 5
<212> TYPE: PRT
<213> ORGANISM: Artificial Sequence
<220> FEATURE:
```

```
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 3

His Xaa Xaa Xaa His
1               5

<210> SEQ ID NO 4
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 4

His Xaa Xaa Xaa Xaa His
1               5

<210> SEQ ID NO 5
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

His Xaa Xaa His His
1               5

<210> SEQ ID NO 6
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 6

His Xaa Xaa Xaa His His
1               5

<210> SEQ ID NO 7
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: Xaa = His [H] or Gln [Q]
<220> FEATURE:
<221> NAME/KEY: misc_feature
<222> LOCATION: (2)..(3)
<223> OTHER INFORMATION: Xaa can be any naturally occurring amino acid

<400> SEQUENCE: 7
```

Xaa Xaa Xaa His His
1               5

<210> SEQ ID NO 8
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: Xaa = His [H] or Gln [Q]
<220> FEATURE:
<221> NAME/KEY: misc_feature
<222> LOCATION: (2)..(4)
<223> OTHER INFORMATION: Xaa can be any naturally occurring amino acid

<400> SEQUENCE: 8

Xaa Xaa Xaa Xaa His His
1               5

<210> SEQ ID NO 9
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 9
aagcagtggt atcaacgcag agtggccatt acggccggg                           39

<210> SEQ ID NO 10
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 10
attctagagg ccgaggcggc cgacatgttt tttttttttt tttttttttt tttttttvn     59

<210> SEQ ID NO 11
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 11
aagcagtggt atcaacgcag agt                                            23

<210> SEQ ID NO 12
<211> LENGTH: 29
<212> TYPE: DNA
<213> ORGANISM: Artificial Sequence
<220> FEATURE:
<223> OTHER INFORMATION: Primer 523
<220> FEATURE:
<221> NAME/KEY: misc_feature
<222> LOCATION: (21)..(21)
<223> OTHER INFORMATION: n is a, c, g, or t

```
<400> SEQUENCE: 12
tggcagcaga tgggctggyt nagycayga                                29

<210> SEQ ID NO 13
<211> LENGTH: 29
<212> TYPE: DNA
<213> ORGANISM: Artificial Sequence
<220> FEATURE:
<223> OTHER INFORMATION: Primer 524
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 13
tggcagcaga tgggctggyt ntcncayga                                29

<210> SEQ ID NO 14
<211> LENGTH: 29
<212> TYPE: DNA
<213> ORGANISM: Artificial Sequence
<220> FEATURE:
<223> OTHER INFORMATION: Primer 525
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 14
tggcagcaga tgggctggyt ngcncayga                                29

<210> SEQ ID NO 15
<211> LENGTH: 10
<212> TYPE: PRT
<213> ORGANISM: Artificial Sequence
<220> FEATURE:
<223> OTHER INFORMATION: conserved amino acid sequence
<220> FEATURE:
<221> NAME/KEY: MISC_FEATURE
<222> LOCATION: (8)..(8)
<223> OTHER INFORMATION: Xaa = Ser (S) or Ala (A)

<400> SEQUENCE: 15

Trp Gln Gln Met Gly Trp Leu Xaa His Asp
1               5                   10

<210> SEQ ID NO 16
<211> LENGTH: 32
<212> TYPE: DNA
<213> ORGANISM: Artificial Sequence
<220> FEATURE:
<223> OTHER INFORMATION: Primer 526
<220> FEATURE:
<221> NAME/KEY: misc_feature
<222> LOCATION: (24)..(24)
<223> OTHER INFORMATION: n is a, c, g, or t

<400> SEQUENCE: 16
ttatggcgcg gcatcgtcgg raanarrtgr tg                            32

<210> SEQ ID NO 17
```

```
<211> LENGTH: 32
<212> TYPE: DNA
<213> ORGANISM: Artificial Sequence
<220> FEATURE:
<223> OTHER INFORMATION: Primer 527
<220> FEATURE:
<221> NAME/KEY: misc_feature
<222> LOCATION: (24)..(24)
<223> OTHER INFORMATION: n is a, c, g, or t

<400> SEQUENCE: 17
ttatggcgcg gcagcgacgg ccanarrtgr tg                                       32

<210> SEQ ID NO 18
<211> LENGTH: 11
<212> TYPE: PRT
<213> ORGANISM: Artificial Sequence
<220> FEATURE:
<223> OTHER INFORMATION: conserved amino acid sequence
<220> FEATURE:
<221> NAME/KEY: MISC_FEATURE
<222> LOCATION: (4)..(4)
<223> OTHER INFORMATION: Xaa = Trp (W) or Phe (F)
<220> FEATURE:
<221> NAME/KEY: MISC_FEATURE
<222> LOCATION: (6)..(6)
<223> OTHER INFORMATION: Xaa = Thr (T) or Ser (S)
<220> FEATURE:
<221> NAME/KEY: MISC_FEATURE
<222> LOCATION: (7)..(7)
<223> OTHER INFORMATION: Xaa = Met (M) or Leu (L)

<400> SEQUENCE: 18

His His Leu Xaa Pro Xaa Xaa Pro Arg His Asn
1               5                   10

<210> SEQ ID NO 19
<211> LENGTH: 30
<212> TYPE: DNA
<213> ORGANISM: Artificial Sequence
<220> FEATURE:
<223> OTHER INFORMATION: Primer 528
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 19
gtggtgctcg atctggtart tnarnccncc                                          30

<210> SEQ ID NO 20
<211> LENGTH: 30
<212> TYPE: DNA
<213> ORGANISM: Artificial Sequence
<220> FEATURE:
<223> OTHER INFORMATION: Primer 529
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
```

```
<222> LOCATION: (28)..(28)
<223> OTHER INFORMATION: n is a, c, g, or t

<400> SEQUENCE: 20
gtggtgctcg atctggtart gnarnccncc                                           30

<210> SEQ ID NO 21
<211> LENGTH: 10
<212> TYPE: PRT
<213> ORGANISM: Artificial Sequence
<220> FEATURE:
<223> OTHER INFORMATION: conserved amino acid sequence
<220> FEATURE:
<221> NAME/KEY: MISC_FEATURE
<222> LOCATION: (4)..(4)
<223> OTHER INFORMATION: Xaa = Asn (N) or His (H)

<400> SEQUENCE: 21

Gly Gly Leu Xaa Tyr Gln Ile Glu His His
1               5                   10

<210> SEQ ID NO 22
<211> LENGTH: 20
<212> TYPE: DNA
<213> ORGANISM: Artificial Sequence
<220> FEATURE:
<223> OTHER INFORMATION: Primer T3

<400> SEQUENCE: 22 attaccctc actaaaggga                                                       20

<210> SEQ ID NO 23
<211> LENGTH: 19
<212> TYPE: DNA
<213> ORGANISM: Artificial Sequence
<220> FEATURE:
<223> OTHER INFORMATION: Primer T7

<400> SEQUENCE: 23
ggaaacagct atgaccatg                                                       19

<210> SEQ ID NO 24
<211> LENGTH: 457
<212> TYPE: PRT
<213> ORGANISM: Mortierella alpina

<400> SEQUENCE: 24

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Ala Phe Lys Val
        115                 120                 125
```

-continued

Ser Phe Asn Leu Cys Ile Trp Gly Leu Ser Thr Val Ile Val Ala Lys
130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
            165                 170                 175

His Gln Val Phe Gln Asp Arg Phe Trp Gly Asp Leu Phe Gly Ala Phe
        180                 185                 190

Leu Gly Gly Val Cys Gln Gly Phe Ser Ser Trp Trp Lys Asp Lys
    195                 200                 205

His Asn Thr His His Ala Ala Pro Asn Val His Gly Glu Asp Pro Asp
210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Val Ser Lys
        435                 440                 445

Ala Ala Ser Lys Met Gly Lys Ala Gln
    450                 455

<210> SEQ ID NO 25
<211> LENGTH: 23
<212> TYPE: DNA
<213> ORGANISM: Artificial Sequence
<220> FEATURE:
<223> OTHER INFORMATION: Primer 535

<400> SEQUENCE: 25
ctcctgcaga gccttctctt cca                                              23

<210> SEQ ID NO 26
<211> LENGTH: 23
<212> TYPE: DNA
<213> ORGANISM: Artificial Sequence -continued

```
<220> FEATURE:
<223> OTHER INFORMATION: Primer 536

<400> SEQUENCE: 26
cctacttcta cttgctgtcc ttg                                              23

<210> SEQ ID NO 27
<211> LENGTH: 22
<212> TYPE: DNA
<213> ORGANISM: Artificial Sequence
<220> FEATURE:
<223> OTHER INFORMATION: Primer 533

<400> SEQUENCE: 27
atgcatgaga agcgcgacga tc                                               22

<210> SEQ ID NO 28
<211> LENGTH: 20
<212> TYPE: DNA
<213> ORGANISM: Artificial Sequence
<220> FEATURE:
<223> OTHER INFORMATION: Primer 534

<400> SEQUENCE: 28
tggaagagaa ggctctgcag                                                  20

<210> SEQ ID NO 29
<211> LENGTH: 19
<212> TYPE: DNA
<213> ORGANISM: Artificial Sequence
<220> FEATURE:
<223> OTHER INFORMATION: Primer 537

<400> SEQUENCE: 29
ctccttgcta tcaccctcg                                                   19

<210> SEQ ID NO 30
<211> LENGTH: 20
<212> TYPE: DNA
<213> ORGANISM: Artificial Sequence
<220> FEATURE:
<223> OTHER INFORMATION: Primer AUAP

<400> SEQUENCE: 30
ggccacgcgt cgactagtac                                                  20

<210> SEQ ID NO 31
<211> LENGTH: 36
<212> TYPE: DNA
<213> ORGANISM: Artificial Sequence
<220> FEATURE:
<223> OTHER INFORMATION: Primer AAP
<220> FEATURE:
<221> NAME/KEY: misc_feature
<222> LOCATION: (24)..(25)
<223> OTHER INFORMATION: n = deoxyinosine
<220> FEATURE:
<221> NAME/KEY: misc_feature
<222> LOCATION: (29)..(30)
<223> OTHER INFORMATION: n = deoxyinosine
<220> FEATURE:
<221> NAME/KEY: misc_feature
<222> LOCATION: (34)..(35)
<223> OTHER INFORMATION: n = deoxyinosine

<400> SEQUENCE: 31
ggccacgcgt cgactagtac gggnngggnn gggnng                                36
```

<210> SEQ ID NO 32
<211> LENGTH: 38
<212> TYPE: DNA
<213> ORGANISM: Artificial Sequence
<220> FEATURE:
<223> OTHER INFORMATION: Primer 539

<400> SEQUENCE: 32

```
aaactaaccc agctctccat ggcgccgaat gtggactc                              38
```

<210> SEQ ID NO 33
<211> LENGTH: 38
<212> TYPE: DNA
<213> ORGANISM: Artificial Sequence
<220> FEATURE:
<223> OTHER INFORMATION: Primer 540

<400> SEQUENCE: 33

```
atccacactt gcggccctat agggattccc caagcttc                              38
```

<210> SEQ ID NO 34
<211> LENGTH: 8423
<212> TYPE: DNA
<213> ORGANISM: Artificial Sequence
<220> FEATURE:
<223> OTHER INFORMATION: Plasmid pY91M

<400> SEQUENCE: 34

```
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aaccccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga agccagttac cttcggaaaa     840
agagttggta gctcttgatc cggcaaacaa accaccgctg gtagcggtgg ttttttttgtt    900
tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatccttttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg gaagggccga gcgcagaagt    1320
ggtcctgcaa cttatccgc ctccatccag tctattaatt gttgccggga agctagagta     1380
agtagttcgc cagttaatag tttgcgcaac gttgttgcca ttgctacagg catcgtggtg    1440
```

```
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
agaagtaagt tggccgcagt gttatcactc atggttatgg cagcactgca taattctctt    1620
actgtcatgc catccgtaag atgcttttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaaagggaat aagggcgaca cggaaatgtt gaatactcat actcttcctt    1980
tttcaatatt attgaagcat ttatcagggt tattgtctca tgagcggata catatttgaa    2040
tgtatttaga aaataaaca ataggggtt ccgcgcacat ttccccgaaa agtgccacct    2100
gacgcgccct gtagcggcgc attaagcgcg gcgggtgtgg tggttacgcg cagcgtgacc    2160
gctacacttg ccagcgccct agcgcccgct cctttcgctt tcttcccttc ctttctcgcc    2220
acgttcgccg gctttccccg tcaagctcta aatcgggggc tccctttagg gttccgattt    2280
agtgctttac ggcacctcga ccccaaaaaa cttgattagg gtgatggttc acgtagtggg    2340
ccatcgccct gatagacggt ttttcgccct ttgacgttgg agtccacgtt ctttaatagt    2400
ggactcttgt tccaaactgg aacaacactc aaccctatct cggtctattc ttttgattta    2460
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatcg gtgcgggcct cttcgctatt acgccagctg gcgaaagggg    2640
gatgtgctgc aaggcgatta agttgggtaa cgccagggtt ttcccagtca cgacgttgta    2700
aaacgacggc cagtgaattg taatacgact cactataggg cgaattgggt accgggcccc    2760
ccctcgaggt cgatggtgtc gataagcttg atatcgaatt catgtcacac aaaccgatct    2820
tcgcctcaag gaaacctaat tctacatccg agagactgcc gagatccagt ctacactgat    2880
taattttcgg gccaataatt taaaaaaatc gtgttatata atattatatg tattatatat    2940
atacatcatg atgatactga cagtcatgtc ccattgctaa atagacagac tccatctgcc    3000
gcctccaact gatgttctca atatttaagg ggtcatctcg cattgtttaa taataaacag    3060
actccatcta ccgcctccaa atgatgttct caaaatatat tgtatgaact tatttttatt    3120
acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
aacagctatt cacacgttac tattgagatt attattggac gagaatcaca cactcaactg    3420
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag atataccaaa gtagcggtat agtggcaatc aaaaagcttc    3600
tctggtgtgc ttctcgtatt tattttatt ctaatgatcc attaaaggta tatatttatt    3660
tcttgttata taatccttt gtttattaca tgggctggat acataaaggt attttgattt    3720 aatttttgc ttaaattcaa tcccccctcg ttcagtgtca actgtaatgg taggaaatta    3780
ccatactttt gaagaagcaa aaaaaatgaa agaaaaaaaa aatcgtattt ccaggttaga    3840
```

```
cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgttttttt ttgtttttttt tttttctaat    4020 gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct gtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg gccagagagc ccttgcaaga    4800
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100 gaggggagc acagtgccgg cgtaggtgaa gtcgtcaatg atgtcgatat gggttttgat    5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg gggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880
ggggcctttt tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
```

```
gtggtgtgac ttgttatagc ctttagagct gcgaaagcgc gtatggattt ggctcatcag    6300
gccagattga gggtctgtgg acacatgtca tgttagtgta cttcaatcgc ccctggata     6360 tagcccgac aataggccgt ggcctcattt ttttgccttc cgcacatttc cattgctcgg     6420
tacccacacc ttgcttctcc tgcacttgcc aaccttaata ctggtttaca ttgaccaaca    6480
tcttacaagc gggggcttg tctagggtat atataaacag tggctctccc aatcggttgc     6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga cgacgcgt tttgtgtaat gacacaatcc      6720
gaaagtcgct agcaacacac actctctaca caaactaacc cagctctcca tgggtggcgg    6780
aggacagcag acagaccgaa tcaccgacac caacggcaga ttcagcagct acacctggga    6840
ggaggtgcag aaacacacca acatggaga tcagtgggtg gtggtggaga ggaaggttta     6900
taacgtcagc cagtgggtga agagacaccc cggaggactg aggatcctcg gacactatgc    6960
tggagaagac gccacggagg cgttcactgc gtttcatcca aaccttcagc tggtgaggaa    7020
atacctgaag ccgctgctaa tcggagagct ggaggcgtct gaacccagtc aggaccggca    7080
gaaaaacgct gctctcgtgg aggatttccg agccctgcgt gagcgtctgg aggctgaagg    7140
ctgttttaaa acgcagccgc tgttttcgc tctgcatttg ggccacattc tgctcctgga    7200
ggccatcgct ttcatgatgg tgtggtattt cggcaccggt tggatcaaca cgctcatcgt    7260
cgctgttatt ctggctactg cacagtcaca agctggatgg ttgcagcatg acttcggtca    7320
tctgtccgtg tttaaaacct ctggaatgaa tcatttggtg cacaaatttg tcatcggaca    7380
cctgaaggga gcgtctgcgg gctggtggaa ccatcggcac ttccagcatc acgctaaacc    7440
caacatcttc aagaaggacc cggacgtcaa catgctgaac gcctttgtgg tgggaaacgt    7500
gcagcccgtg gagtatggcg ttaagaagat caagcatctg ccctacaacc atcagcacaa    7560
gtacttcttc ttcattggtc ctcccctgct catcccagtg tatttccagt tccaaatctt    7620
tcacaatatg atcagtcatg gcatgtgggt ggacctgctg tggtgtatca gctactacgt    7680
ccgatacttc ctttgttaca cgcagttcta cggcgtcttt tgggctatta tcctctttaa    7740
tttcgtcagg tttatggaga gccactggtt tgtttgggtc acacagatga gccacatccc    7800
catgaacatt gactatgaga aaatcagga ctggctcagc atgcagctgg tcgcgacctg     7860
taacatcgag cagtctgcct tcaacgactg gttcagcgga cacctcaact tccagatcga    7920
gcatcatctc tttcccacag tgcctcggca caactactgg cgcgccgctc cacgggtgcg    7980
agcgttgtgt gagaaatacg gagtcaaata ccaagagaag accttgtacg gagcatttgc    8040
ggatatcatt aggtctttgg agaaatctgg cgagctctgg ctggatgcgt atctcaacaa    8100
ataagcggcc gcaagtgtgg atggggaagt gagtgcccgg ttctgtgtgc acaattggca    8160
atccaagatg gatggattca acacagggat atagcgagct acgtggtggt gcgaggatat    8220
agcaacggat atttatgttt gacacttgag aatgtacgat acaagcactg tccaagtaca    8280
atactaaaca tactgtacat actccatactc gtacccgggc aacggtttca cttgagtgca    8340
gtggctagtg ctcttactcg tacagtgtgc aatactgcgt atcatagtct tgatgtata    8400 tcgtattcat tcatgttagt tgc                                             8423
```

<210> SEQ ID NO 35
<211> LENGTH: 20
<212> TYPE: DNA
<213> ORGANISM: Artificial Sequence

```
<220> FEATURE:
<223> OTHER INFORMATION: Primer 373

<400> SEQUENCE: 35
cgcgttttgt gtaatgacac                                                  20

<210> SEQ ID NO 36
<211> LENGTH: 20
<212> TYPE: DNA
<213> ORGANISM: Artificial Sequence
<220> FEATURE:
<223> OTHER INFORMATION: Primer 507

<400> SEQUENCE: 36
acacagaacc gggcactcac                                                  20

<210> SEQ ID NO 37
<211> LENGTH: 477
<212> TYPE: PRT
<213> ORGANISM: Phaeodactylum tricornutum
<220> FEATURE:
<221> NAME/KEY: MISC_FEATURE
<222> LOCATION: (1)..(477)
<223> OTHER INFORMATION: GenBank Accession No. AAL92563 (gi_19879689)

<400> SEQUENCE: 37
```

| Met | Gly | Lys | Gly | Gly | Asp | Ala | Arg | Ala | Ser | Lys | Gly | Ser | Thr | Ala | Ala |
|---|---|---|---|---|---|---|---|---|---|---|---|---|---|---|---|
| 1 | | | | 5 | | | | | 10 | | | | | 15 | |

| Arg | Lys | Ile | Ser | Trp | Gln | Glu | Val | Lys | Thr | His | Ala | Ser | Pro | Glu | Asp |
|---|---|---|---|---|---|---|---|---|---|---|---|---|---|---|---|
| | | | 20 | | | | | 25 | | | | | 30 | | |

| Ala | Trp | Ile | Ile | His | Ser | Asn | Lys | Val | Tyr | Asp | Val | Ser | Asn | Trp | His |
|---|---|---|---|---|---|---|---|---|---|---|---|---|---|---|---|
| | | 35 | | | | | 40 | | | | | 45 | | | |

| Glu | His | Pro | Gly | Gly | Ala | Val | Ile | Phe | Thr | His | Ala | Gly | Asp | Asp | Met |
|---|---|---|---|---|---|---|---|---|---|---|---|---|---|---|---|
| | 50 | | | | | 55 | | | | | 60 | | | | |

| Thr | Asp | Ile | Phe | Ala | Ala | Phe | His | Ala | Pro | Gly | Ser | Gln | Ser | Leu | Met |
|---|---|---|---|---|---|---|---|---|---|---|---|---|---|---|---|
| 65 | | | | | 70 | | | | | 75 | | | | | 80 |

| Lys | Lys | Phe | Tyr | Ile | Gly | Glu | Leu | Leu | Pro | Glu | Thr | Thr | Gly | Lys | Glu |
|---|---|---|---|---|---|---|---|---|---|---|---|---|---|---|---|
| | | | | 85 | | | | | 90 | | | | | 95 | |

| Pro | Gln | Gln | Ile | Ala | Phe | Glu | Lys | Gly | Tyr | Arg | Asp | Leu | Arg | Ser | Lys |
|---|---|---|---|---|---|---|---|---|---|---|---|---|---|---|---|
| | | | 100 | | | | | 105 | | | | | 110 | | |

| Leu | Ile | Met | Met | Gly | Met | Phe | Lys | Ser | Asn | Lys | Trp | Phe | Tyr | Val | Tyr |
|---|---|---|---|---|---|---|---|---|---|---|---|---|---|---|---|
| | | 115 | | | | | 120 | | | | | 125 | | | |

| Lys | Cys | Leu | Ser | Asn | Met | Ala | Ile | Trp | Ala | Ala | Ala | Cys | Ala | Leu | Val |
|---|---|---|---|---|---|---|---|---|---|---|---|---|---|---|---|
| | 130 | | | | | 135 | | | | | 140 | | | | |

| Phe | Tyr | Ser | Asp | Arg | Phe | Trp | Val | His | Leu | Ala | Ser | Ala | Val | Met | Leu |
|---|---|---|---|---|---|---|---|---|---|---|---|---|---|---|---|
| 145 | | | | | 150 | | | | | 155 | | | | | 160 |

| Gly | Thr | Phe | Phe | Gln | Gln | Ser | Gly | Trp | Leu | Ala | His | Asp | Phe | Leu | His |
|---|---|---|---|---|---|---|---|---|---|---|---|---|---|---|---|
| | | | | 165 | | | | | 170 | | | | | 175 | |

| His | Gln | Val | Phe | Thr | Lys | Arg | Lys | His | Gly | Asp | Leu | Gly | Gly | Leu | Phe |
|---|---|---|---|---|---|---|---|---|---|---|---|---|---|---|---|
| | | | 180 | | | | | 185 | | | | | 190 | | |

| Trp | Gly | Asn | Leu | Met | Gln | Gly | Tyr | Ser | Val | Gln | Trp | Trp | Lys | Asn | Lys |
|---|---|---|---|---|---|---|---|---|---|---|---|---|---|---|---|
| | | 195 | | | | | 200 | | | | | 205 | | | |

| His | Asn | Gly | His | His | Ala | Val | Pro | Asn | Leu | His | Cys | Ser | Ser | Ala | Val |
|---|---|---|---|---|---|---|---|---|---|---|---|---|---|---|---|
| | 210 | | | | | 215 | | | | | 220 | | | | |

| Ala | Gln | Asp | Gly | Asp | Pro | Asp | Ile | Asp | Thr | Met | Pro | Leu | Leu | Ala | Trp |
|---|---|---|---|---|---|---|---|---|---|---|---|---|---|---|---|
| 225 | | | | | 230 | | | | | 235 | | | | | 240 |

| Ser | Val | Gln | Gln | Ala | Gln | Ser | Tyr | Arg | Glu | Leu | Gln | Ala | Asp | Gly | Lys |
|---|---|---|---|---|---|---|---|---|---|---|---|---|---|---|---|
| | | | | 245 | | | | | 250 | | | | | 255 | |

| Asp | Ser | Gly | Leu | Val | Lys | Phe | Met | Ile | Arg | Asn | Gln | Ser | Tyr | Phe | Tyr |
|---|---|---|---|---|---|---|---|---|---|---|---|---|---|---|---|

```
                 260                 265                 270
Phe Pro Ile Leu Leu Leu Ala Arg Leu Ser Trp Leu Asn Glu Ser Phe
            275                 280                 285
Lys Cys Ala Phe Gly Leu Gly Ala Ala Ser Glu Asn Ala Ala Leu Glu
        290                 295                 300
Leu Lys Ala Lys Gly Leu Gln Tyr Pro Leu Leu Glu Lys Ala Gly Ile
305                 310                 315                 320
Leu Leu His Tyr Ala Trp Met Leu Thr Val Ser Gly Phe Gly Arg
            325                 330                 335
Phe Ser Phe Ala Tyr Thr Ala Phe Tyr Phe Leu Thr Ala Thr Ala Ser
            340                 345                 350
Cys Gly Phe Leu Leu Ala Ile Val Phe Gly Leu Gly His Asn Gly Met
            355                 360                 365
Ala Thr Tyr Asn Ala Asp Ala Arg Pro Asp Phe Trp Lys Leu Gln Val
            370                 375                 380
Thr Thr Thr Arg Asn Val Thr Gly Gly His Gly Phe Pro Gln Ala Phe
385                 390                 395                 400
Val Asp Trp Phe Cys Gly Gly Leu Gln Tyr Gln Val Asp His His Leu
            405                 410                 415
Phe Pro Ser Leu Pro Arg His Asn Leu Ala Lys Thr His Ala Leu Val
            420                 425                 430
Glu Ser Phe Cys Lys Glu Trp Gly Val Gln Tyr His Glu Ala Asp Leu
            435                 440                 445
Val Asp Gly Thr Met Glu Val Leu His His Leu Gly Ser Val Ala Gly
            450                 455                 460
Glu Phe Val Val Asp Phe Val Arg Asp Gly Pro Ala Met
465                 470                 475

<210> SEQ ID NO 38
<211> LENGTH: 525
<212> TYPE: PRT
<213> ORGANISM: Physcomitrella patens
<220> FEATURE:
<221> NAME/KEY: MISC_FEATURE
<222> LOCATION: (1)..(525)
<223> OTHER INFORMATION: GenBank Accession No. CAA11033 (gi_3790209)

<400> SEQUENCE: 38

Met Val Phe Ala Gly Gly Gly Leu Gln Gln Gly Ser Leu Glu Glu Asn
1               5                   10                  15
Ile Asp Val Glu His Ile Ala Ser Met Ser Leu Phe Ser Asp Phe Phe
            20                  25                  30
Ser Tyr Val Ser Ser Thr Val Gly Ser Trp Ser Val His Ser Ile Gln
        35                  40                  45
Pro Leu Lys Arg Leu Thr Ser Lys Lys Arg Val Ser Glu Ser Ala Ala
    50                  55                  60
Val Gln Cys Ile Ser Ala Glu Val Gln Arg Asn Ser Ser Thr Gln Gly
65                  70                  75                  80
Thr Ala Glu Ala Leu Ala Glu Ser Val Val Lys Pro Thr Arg Arg Arg
                85                  90                  95
Ser Ser Gln Trp Lys Lys Ser Thr His Pro Leu Ser Glu Val Ala Val
            100                 105                 110
His Asn Lys Pro Ser Asp Cys Trp Ile Val Val Lys Asn Lys Val Tyr
        115                 120                 125
Asp Val Ser Asn Phe Ala Asp Glu His Pro Gly Gly Ser Val Ile Ser
    130                 135                 140
```

| Thr | Tyr | Phe | Gly | Arg | Asp | Gly | Thr | Asp | Val | Phe | Ser | Ser | Phe | His | Ala |
| 145 | | | | 150 | | | | | 155 | | | | | | 160 |

| Ala | Ser | Thr | Trp | Lys | Ile | Leu | Gln | Asp | Phe | Tyr | Ile | Gly | Asp | Val | Glu |
| | | | | 165 | | | | | 170 | | | | | 175 | |

| Arg | Val | Glu | Pro | Thr | Pro | Glu | Leu | Leu | Lys | Asp | Phe | Arg | Glu | Met | Arg |
| | | | 180 | | | | | 185 | | | | | 190 | | |

| Ala | Leu | Phe | Leu | Arg | Glu | Gln | Leu | Phe | Lys | Ser | Ser | Lys | Leu | Tyr | Tyr |
| | | 195 | | | | | 200 | | | | | 205 | | | |

| Val | Met | Lys | Leu | Leu | Thr | Asn | Val | Ala | Ile | Phe | Ala | Ala | Ser | Ile | Ala |
| | 210 | | | | | 215 | | | | | 220 | | | | |

| Ile | Ile | Cys | Trp | Ser | Lys | Thr | Ile | Ser | Ala | Val | Leu | Ala | Ser | Ala | Cys |
| 225 | | | | | 230 | | | | | 235 | | | | | 240 |

| Met | Met | Ala | Leu | Cys | Phe | Gln | Gln | Cys | Gly | Trp | Leu | Ser | His | Asp | Phe |
| | | | | 245 | | | | | 250 | | | | | 255 | |

| Leu | His | Asn | Gln | Val | Phe | Glu | Thr | Arg | Trp | Leu | Asn | Glu | Val | Val | Gly |
| | | | 260 | | | | | 265 | | | | | 270 | | |

| Tyr | Val | Ile | Gly | Asn | Ala | Val | Leu | Gly | Phe | Ser | Thr | Gly | Trp | Trp | Lys |
| | | 275 | | | | | 280 | | | | | 285 | | | |

| Glu | Lys | His | Asn | Leu | His | Ala | Ala | Pro | Asn | Glu | Cys | Asp | Gln | Thr |
| | 290 | | | | | 295 | | | | | 300 | | | | |

| Tyr | Gln | Pro | Ile | Asp | Glu | Asp | Ile | Asp | Thr | Leu | Pro | Leu | Ile | Ala | Trp |
| 305 | | | | | 310 | | | | | 315 | | | | | 320 |

| Ser | Lys | Asp | Ile | Leu | Ala | Thr | Val | Glu | Asn | Lys | Thr | Phe | Leu | Arg | Ile |
| | | | | 325 | | | | | 330 | | | | | 335 | |

| Leu | Gln | Tyr | Gln | His | Leu | Phe | Phe | Met | Gly | Leu | Leu | Phe | Ala | Arg |
| | | | 340 | | | | | 345 | | | | | 350 | | |

| Gly | Ser | Trp | Leu | Phe | Trp | Ser | Trp | Arg | Tyr | Thr | Ser | Thr | Ala | Val | Leu |
| | | | 355 | | | | | 360 | | | | | 365 | | |

| Ser | Pro | Val | Asp | Arg | Leu | Leu | Glu | Lys | Gly | Thr | Val | Leu | Phe | His | Tyr |
| | 370 | | | | | 375 | | | | | 380 | | | | |

| Phe | Trp | Phe | Val | Gly | Thr | Ala | Cys | Tyr | Leu | Leu | Pro | Gly | Trp | Lys | Pro |
| 385 | | | | | 390 | | | | | 395 | | | | | 400 |

| Leu | Val | Trp | Met | Ala | Val | Thr | Glu | Leu | Met | Ser | Gly | Met | Leu | Leu | Gly |
| | | | | 405 | | | | | 410 | | | | | 415 | |

| Phe | Val | Phe | Val | Leu | Ser | His | Asn | Gly | Met | Glu | Val | Tyr | Asn | Ser | Ser |
| | | | 420 | | | | | 425 | | | | | 430 | | |

| Lys | Glu | Phe | Val | Ser | Ala | Gln | Ile | Val | Ser | Thr | Arg | Asp | Ile | Lys | Gly |
| | | 435 | | | | | 440 | | | | | 445 | | | |

| Asn | Ile | Phe | Asn | Asp | Trp | Phe | Thr | Gly | Gly | Leu | Asn | Arg | Gln | Ile | Glu |
| | 450 | | | | | 455 | | | | | 460 | | | | |

| His | His | Leu | Phe | Pro | Thr | Met | Pro | Arg | His | Asn | Leu | Asn | Lys | Ile | Ala |
| 465 | | | | | 470 | | | | | 475 | | | | | 480 |

| Pro | Arg | Val | Glu | Val | Phe | Cys | Lys | Lys | His | Gly | Leu | Val | Tyr | Glu | Asp |
| | | | | 485 | | | | | 490 | | | | | 495 | |

| Val | Ser | Ile | Ala | Thr | Gly | Thr | Cys | Lys | Val | Leu | Lys | Ala | Leu | Lys | Glu |
| | | | 500 | | | | | 505 | | | | | 510 | | |

| Val | Ala | Glu | Ala | Ala | Ala | Glu | Gln | His | Ala | Thr | Thr | Ser |
| | | 515 | | | | | 520 | | | | | 525 |

<210> SEQ ID NO 39
<211> LENGTH: 481
<212> TYPE: PRT
<213> ORGANISM: Marchantia polymorpha
<220> FEATURE:
<221> NAME/KEY: MISC_FEATURE
<222> LOCATION: (1)..(481)

<223> OTHER INFORMATION: GenBank Accession No. AAT85661 (gi_50882491)

<400> SEQUENCE: 39

| | | | | | | | | | | | | | | |
|---|---|---|---|---|---|---|---|---|---|---|---|---|---|---|
| Met | Ala | Ser | Ser | Thr | Thr | Ala | Val | Lys | Gln | Ser | Gly | Gly | Leu |
| 1 | | | | 5 | | | | | 10 | | | | | 15 |
| Trp | Ser | Lys | Trp | Gly | Thr | Gly | Ser | Asn | Leu | Ser | Phe | Val | Ser | Arg | Lys |
| | | | 20 | | | | | 25 | | | | | 30 |
| Glu | Gln | Gln | Gln | Gln | Gln | Gln | Gln | Ser | Ser | Pro | Glu | Ala | Ser | Thr | Pro |
| | | | 35 | | | | | 40 | | | | | 45 |
| Ala | Ala | Gln | Gln | Glu | Lys | Ser | Ile | Ser | Arg | Glu | Ser | Ile | Pro | Glu | Gly |
| | 50 | | | | | 55 | | | | | 60 |
| Phe | Leu | Thr | Val | Glu | Glu | Val | Ser | Lys | His | Asp | Asn | Pro | Ser | Asp | Cys |
| 65 | | | | | 70 | | | | | 75 | | | | | 80 |
| Trp | Ile | Val | Ile | Asn | Asp | Lys | Val | Tyr | Asp | Val | Ser | Ala | Phe | Gly | Lys |
| | | | | 85 | | | | | 90 | | | | | 95 |
| Thr | His | Pro | Gly | Gly | Pro | Val | Ile | Phe | Thr | Gln | Ala | Gly | Arg | Asp | Ala |
| | | | 100 | | | | | 105 | | | | | 110 |
| Thr | Asp | Ser | Phe | Lys | Val | Phe | His | Ser | Ala | Lys | Ala | Trp | Gln | Phe | Leu |
| | | | 115 | | | | | 120 | | | | | 125 |
| Gln | Asp | Leu | Tyr | Ile | Gly | Asp | Leu | Tyr | Asn | Ala | Glu | Pro | Val | Ser | Glu |
| | 130 | | | | | 135 | | | | | 140 |
| Leu | Val | Lys | Asp | Tyr | Arg | Asp | Leu | Arg | Thr | Ala | Phe | Met | Arg | Ser | Gln |
| 145 | | | | | 150 | | | | | 155 | | | | | 160 |
| Leu | Phe | Lys | Ser | Ser | Lys | Met | Tyr | Tyr | Val | Thr | Lys | Cys | Val | Thr | Asn |
| | | | | 165 | | | | | 170 | | | | | 175 |
| Phe | Ala | Ile | Leu | Ala | Ala | Ser | Leu | Ala | Val | Ile | Ala | Trp | Ser | Gln | Thr |
| | | | 180 | | | | | 185 | | | | | 190 |
| Tyr | Leu | Ala | Val | Leu | Cys | Ser | Ser | Phe | Leu | Leu | Ala | Leu | Phe | Trp | Gln |
| | | 195 | | | | | 200 | | | | | 205 |
| Gln | Cys | Gly | Trp | Leu | Ser | His | Asp | Phe | Leu | His | His | Gln | Val | Thr | Glu |
| | 210 | | | | | 215 | | | | | 220 |
| Asn | Arg | Ser | Leu | Asn | Thr | Tyr | Phe | Gly | Gly | Leu | Phe | Trp | Gly | Asn | Phe |
| 225 | | | | | 230 | | | | | 235 | | | | | 240 |
| Ala | Gln | Gly | Tyr | Ser | Val | Gly | Trp | Trp | Lys | Thr | Lys | His | Asn | Val | His |
| | | | 245 | | | | | 250 | | | | | 255 |
| His | Ala | Ala | Thr | Asn | Glu | Cys | Asp | Asp | Lys | Tyr | Gln | Pro | Ile | Asp | Pro |
| | | | 260 | | | | | 265 | | | | | 270 |
| Asp | Ile | Asp | Thr | Val | Pro | Leu | Leu | Ala | Trp | Ser | Lys | Glu | Ile | Leu | Ala |
| | | 275 | | | | | 280 | | | | | 285 |
| Thr | Val | Asp | Asp | Gln | Phe | Phe | Arg | Ser | Ile | Ile | Ser | Val | Gln | His | Leu |
| | 290 | | | | | 295 | | | | | 300 |
| Leu | Phe | Phe | Pro | Leu | Leu | Phe | Leu | Ala | Arg | Phe | Ser | Trp | Leu | His | Ser |
| 305 | | | | | 310 | | | | | 315 | | | | | 320 |
| Ser | Trp | Ala | His | Ala | Ser | Asn | Phe | Glu | Met | Pro | Arg | Tyr | Met | Arg | Trp |
| | | | | 325 | | | | | 330 | | | | | 335 |
| Ala | Glu | Lys | Ala | Ser | Leu | Leu | Gly | His | Tyr | Gly | Ala | Ser | Ile | Gly | Ala |
| | | | 340 | | | | | 345 | | | | | 350 |
| Ala | Phe | Tyr | Ile | Leu | Pro | Ile | Pro | Gln | Ala | Ile | Cys | Trp | Leu | Phe | Leu |
| | | 355 | | | | | 360 | | | | | 365 |
| Ser | Gln | Leu | Phe | Cys | Gly | Ala | Leu | Leu | Ser | Ile | Val | Phe | Val | Ile | Ser |
| | 370 | | | | | 375 | | | | | 380 |
| His | Asn | Gly | Met | Asp | Val | Tyr | Asn | Asp | Pro | Arg | Asp | Phe | Val | Thr | Ala |
| 385 | | | | | 390 | | | | | 395 | | | | | 400 |
| Gln | Val | Thr | Ser | Thr | Arg | Asn | Ile | Glu | Gly | Asn | Phe | Phe | Asn | Asp | Trp |

```
                       405                 410                 415
Phe Thr Gly Gly Leu Asn Arg Gln Ile Glu His His Leu Phe Pro Ser
            420                 425                 430

Leu Pro Arg His Asn Leu Ala Lys Val Ala Pro His Val Lys Ala Leu
            435                 440                 445

Cys Ala Lys His Gly Leu His Tyr Glu Glu Leu Ser Leu Gly Thr Gly
            450                 455                 460

Val Cys Arg Val Phe Asn Arg Leu Val Glu Val Ala Tyr Ala Ala Lys
465                 470                 475                 480

Val

<210> SEQ ID NO 40
<211> LENGTH: 457
<212> TYPE: PRT
<213> ORGANISM: Mortierella alpina
<220> FEATURE:
<221> NAME/KEY: MISC_FEATURE
<222> LOCATION: (1)..(457)
<223> OTHER INFORMATION: GenBank Accession No. AAL73947 (gi_18483175)

<400> SEQUENCE: 40

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Ala Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Phe Ile Val Ala Lys
    130                 135                 140

Trp Gly Gln Thr Ser Thr Leu Ala Asn Glu Leu Ser Ala Ala Leu Leu
145                 150                 155                 160

Gly Leu Phe Trp Gln Gln Arg Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Asp Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
```

```
                275                 280                 285
Gln Ala His Lys Pro Ser Gly Ala Arg Val Pro Ile Ser Leu Val Glu
    290                 295                 300
Gln Leu Ser Leu Ala Met His Trp Thr Trp Tyr Leu Ala Thr Met Phe
305                 310                 315                 320
Leu Phe Ile Lys Asp Pro Val Asn Met Met Val Tyr Phe Leu Val Ser
                325                 330                 335
Gln Ala Val Cys Gly Asn Leu Leu Ala Ile Val Phe Ser Leu Asn His
                340                 345                 350
Asn Gly Met Pro Val Ile Ser Lys Glu Glu Ala Val Asp Met Asp Phe
                355                 360                 365
Phe Thr Lys Gln Ile Ile Thr Gly Arg Asp Val His Pro Gly Leu Phe
370                 375                 380
Ala Asn Trp Phe Thr Gly Gly Leu Asn Tyr Gln Ile Glu His His Leu
385                 390                 395                 400
Phe Pro Ser Met Pro Arg His Asn Phe Ser Lys Ile Gln Pro Ala Val
                405                 410                 415
Glu Thr Leu Cys Lys Lys Tyr Gly Val Arg Tyr His Thr Thr Gly Met
                420                 425                 430
Ile Glu Gly Thr Ala Glu Val Phe Ser Arg Leu Asn Glu Val Ser Lys
                435                 440                 445
Ala Ala Ser Lys Met Gly Lys Ala Gln
    450                 455

<210> SEQ ID NO 41
<211> LENGTH: 419
<212> TYPE: PRT
<213> ORGANISM: Euglena gracilis
<220> FEATURE:
<221> NAME/KEY: MISC_FEATURE
<222> LOCATION: (1)..(419)
<223> OTHER INFORMATION: GenBank Accession No. AAD45877 (gi_5639724)

<400> SEQUENCE: 41

Met Lys Ser Lys Arg Gln Ala Leu Ser Pro Leu Gln Leu Met Glu Gln
1               5                   10                  15
Thr Tyr Asp Val Val Asn Phe His Pro Gly Gly Ala Glu Ile Ile Glu
                20                  25                  30
Asn Tyr Gln Gly Arg Asp Ala Thr Asp Ala Phe Met Val Met His Phe
            35                  40                  45
Gln Glu Ala Phe Asp Lys Leu Lys Arg Met Pro Lys Ile Asn Pro Ser
        50                  55                  60
Phe Glu Leu Pro Pro Gln Ala Ala Val Asn Glu Ala Gln Glu Asp Phe
65                  70                  75                  80
Arg Lys Leu Arg Glu Glu Leu Ile Ala Thr Gly Met Phe Asp Ala Ser
                85                  90                  95
Pro Leu Trp Tyr Ser Tyr Lys Ile Ser Thr Thr Leu Gly Leu Gly Val
                100                 105                 110
Leu Gly Tyr Phe Leu Met Val Gln Tyr Gln Met Tyr Phe Ile Gly Ala
            115                 120                 125
Val Leu Leu Gly Met His Tyr Gln Gln Met Gly Trp Leu Ser His Asp
        130                 135                 140
Ile Cys His His Gln Thr Phe Lys Asn Arg Asn Trp Asn Asn Leu Val
145                 150                 155                 160
Gly Leu Val Phe Gly Asn Gly Leu Gln Gly Phe Ser Val Thr Cys Trp
                165                 170                 175
```

-continued

```
Lys Asp Arg His Asn Ala His His Ser Ala Thr Asn Val Gln Gly His
            180                 185                 190

Asp Pro Asp Ile Asp Asn Leu Pro Leu Ala Trp Ser Glu Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu
```

<210> SEQ ID NO 42
<211> LENGTH: 1416
<212> TYPE: DNA
<213> ORGANISM: Porphyridium cruentum
<220> FEATURE:
<221> NAME/KEY: CDS
<222> LOCATION: (1)..(1416)
<223> OTHER INFORMATION: variant of SEQ ID NO:1

<400> SEQUENCE: 42

```
atg gcg ccg aat gtg gac tcc gga agc aag gac cgc ggc gtg agc gcg      48
Met Ala Pro Asn Val Asp Ser Gly Ser Lys Asp Arg Gly Val Ser Ala
1               5                   10                  15 gtc aaa gaa gta gtc tct ggc gcg acg gcc aac gcg ctg agt ccg gcc      96
Val Lys Glu Val Val Ser Gly Ala Thr Ala Asn Ala Leu Ser Pro Ala
                20                  25                  30 gag cgc gtg gtg acc agg aag gag ctc gcg ggg cac gcc tca agg gag     144
Glu Arg Val Val Thr Arg Lys Glu Leu Ala Gly His Ala Ser Arg Glu
            35                  40                  45 tcg gtg tgg att gcg gtg aac ggc cgt gtg tac gat gtg acc ggc ttt     192
Ser Val Trp Ile Ala Val Asn Gly Arg Val Tyr Asp Val Thr Gly Phe
        50                  55                  60 gag aac gtt cac cct ggc ggc gag atc att ctg acc gcc gcc ggg cag     240
Glu Asn Val His Pro Gly Gly Glu Ile Ile Leu Thr Ala Ala Gly Gln
65                  70                  75                  80 gac gca acg gac gtg ttt gcc gcg ttt cac acg ccc gcc acg tgg aaa     288
```

-continued

| | | | | | | | | | | | | | | | | |
|---|---|---|---|---|---|---|---|---|---|---|---|---|---|---|---|---|
| | Asp | Ala | Thr | Asp | Val | Phe | Ala | Ala | Phe | His | Thr | Pro | Ala | Thr | Trp | Lys |
| | | | | 85 | | | | | 90 | | | | | 95 | | |

| atg | atg | ccg | cag | ttc | ctc | gtg | gga | aac | ctc | gag | gag | gac | gcg | ctc | tct | 336 |
|---|---|---|---|---|---|---|---|---|---|---|---|---|---|---|---|---|
| Met | Met | Pro | Gln | Phe | Leu | Val | Gly | Asn | Leu | Glu | Glu | Asp | Ala | Leu | Ser | |
| | | | 100 | | | | | 105 | | | | | 110 | | | |

| gcc | aaa | ccg | tct | aag | cag | ctt | aat | ggg | cat | tcg | cca | cac | gag | tac | caa | 384 |
|---|---|---|---|---|---|---|---|---|---|---|---|---|---|---|---|---|
| Ala | Lys | Pro | Ser | Lys | Gln | Leu | Asn | Gly | His | Ser | Pro | His | Glu | Tyr | Gln | |
| | | | 115 | | | | | 120 | | | | | 125 | | | |

| gct | gat | atc | cga | aag | atg | cgt | gcg | gaa | ctt | gtc | aag | ctg | cgc | gcg | ttc | 432 |
|---|---|---|---|---|---|---|---|---|---|---|---|---|---|---|---|---|
| Ala | Asp | Ile | Arg | Lys | Met | Arg | Ala | Glu | Leu | Val | Lys | Leu | Arg | Ala | Phe | |
| | 130 | | | | | 135 | | | | | 140 | | | | | |

| gac | tcg | aac | aag | ttc | ttc | tac | ctg | ttc | aag | ttc | ctg | tcc | acg | tct | gcg | 480 |
|---|---|---|---|---|---|---|---|---|---|---|---|---|---|---|---|---|
| Asp | Ser | Asn | Lys | Phe | Phe | Tyr | Leu | Phe | Lys | Phe | Leu | Ser | Thr | Ser | Ala | |
| 145 | | | | | 150 | | | | | 155 | | | | | 160 | |

| att | tgc | gcc | ctc | ttg | gtg | gtc | atg | gcg | ctc | ggc | atg | aag | gac | tcg | atg | 528 |
|---|---|---|---|---|---|---|---|---|---|---|---|---|---|---|---|---|
| Ile | Cys | Ala | Leu | Leu | Val | Val | Met | Ala | Leu | Gly | Met | Lys | Asp | Ser | Met | |
| | | | | 165 | | | | | 170 | | | | | 175 | | |

| atc | gtc | acg | gcg | ctc | gcc | gcg | ttc | acc | atg | gca | ctc | ttc | tgg | cag | cag | 576 |
|---|---|---|---|---|---|---|---|---|---|---|---|---|---|---|---|---|
| Ile | Val | Thr | Ala | Leu | Ala | Ala | Phe | Thr | Met | Ala | Leu | Phe | Trp | Gln | Gln | |
| | | | 180 | | | | | 185 | | | | | 190 | | | |

| tgc | ggc | tgg | ctc | gct | cac | gac | ttt | ctg | cac | cat | cag | gtg | ttc | aag | aac | 624 |
|---|---|---|---|---|---|---|---|---|---|---|---|---|---|---|---|---|
| Cys | Gly | Trp | Leu | Ala | His | Asp | Phe | Leu | His | His | Gln | Val | Phe | Lys | Asn | |
| | | | 195 | | | | | 200 | | | | | 205 | | | |

| agg | gtg | ttc | aac | aac | ctg | gtc | ggt | ctt | gtt | gtt | ggt | aat | gtc | tat | cag | 672 |
|---|---|---|---|---|---|---|---|---|---|---|---|---|---|---|---|---|
| Arg | Val | Phe | Asn | Asn | Leu | Val | Gly | Leu | Val | Val | Gly | Asn | Val | Tyr | Gln | |
| | 210 | | | | | 215 | | | | | 220 | | | | | |

| ggc | ttt | tcg | gta | tcc | tgg | tgg | aag | atg | aag | cac | aac | cac | cac | cac | gcc | 720 |
|---|---|---|---|---|---|---|---|---|---|---|---|---|---|---|---|---|
| Gly | Phe | Ser | Val | Ser | Trp | Trp | Lys | Met | Lys | His | Asn | His | His | His | Ala | |
| 225 | | | | | 230 | | | | | 235 | | | | | 240 | |

| gct | cca | aac | gtg | acg | tca | acg | gcc | gct | ggg | cca | gac | cca | gac | atc | gac | 768 |
|---|---|---|---|---|---|---|---|---|---|---|---|---|---|---|---|---|
| Ala | Pro | Asn | Val | Thr | Ser | Thr | Ala | Ala | Gly | Pro | Asp | Pro | Asp | Ile | Asp | |
| | | | | 245 | | | | | 250 | | | | | 255 | | |

| act | gtg | ccc | gtg | ctc | tcg | tgg | agc | gag | aaa | ctc | atc | gag | ggt | gat | agc | 816 |
|---|---|---|---|---|---|---|---|---|---|---|---|---|---|---|---|---|
| Thr | Val | Pro | Val | Leu | Ser | Trp | Ser | Glu | Lys | Leu | Ile | Glu | Gly | Asp | Ser | |
| | | | 260 | | | | | 265 | | | | | 270 | | | |

| aag | gag | atg | gag | gat | ctg | ccc | atg | ttc | ctc | atg | aag | aac | cag | aag | atc | 864 |
|---|---|---|---|---|---|---|---|---|---|---|---|---|---|---|---|---|
| Lys | Glu | Met | Glu | Asp | Leu | Pro | Met | Phe | Leu | Met | Lys | Asn | Gln | Lys | Ile | |
| | 275 | | | | | 280 | | | | | 285 | | | | | |

| ttt | tac | tgg | ccg | gtt | ctg | tgc | gtg | gcg | cgc | atc | agc | tgg | ctc | ctg | cag | 912 |
|---|---|---|---|---|---|---|---|---|---|---|---|---|---|---|---|---|
| Phe | Tyr | Trp | Pro | Val | Leu | Cys | Val | Ala | Arg | Ile | Ser | Trp | Leu | Leu | Gln | |
| 290 | | | | | 295 | | | | | 300 | | | | | | |

| agc | ctt | ctc | ttc | cag | cgc | gcg | ccg | gtc | tgg | aac | ttt | gtg | ggc | gga | aac | 960 |
|---|---|---|---|---|---|---|---|---|---|---|---|---|---|---|---|---|
| Ser | Leu | Leu | Phe | Gln | Arg | Ala | Pro | Val | Trp | Asn | Phe | Val | Gly | Gly | Asn | |
| 305 | | | | | 310 | | | | | 315 | | | | | 320 | |

| agc | tgg | cgc | gcg | gtg | gag | acc | gtc | gcg | ctt | ctc | atg | cat | cac | ggc | gcc | 1008 |
|---|---|---|---|---|---|---|---|---|---|---|---|---|---|---|---|---|
| Ser | Trp | Arg | Ala | Val | Glu | Thr | Val | Ala | Leu | Leu | Met | His | His | Gly | Ala | |
| | | | 325 | | | | | 330 | | | | | 335 | | | |

| tac | ttc | tac | ttg | ctg | tcc | ttg | ctc | aag | agc | tgg | gtc | cat | gtc | gtg | ctc | 1056 |
|---|---|---|---|---|---|---|---|---|---|---|---|---|---|---|---|---|
| Tyr | Phe | Tyr | Leu | Leu | Ser | Leu | Leu | Lys | Ser | Trp | Val | His | Val | Val | Leu | |
| | | | 340 | | | | | 345 | | | | | 350 | | | |

| ttt | ttg | gtg | gtg | agc | cag | gcg | atg | ggt | ggt | gtg | cta | ctc | ggc | gtc | gtg | 1104 |
|---|---|---|---|---|---|---|---|---|---|---|---|---|---|---|---|---|
| Phe | Leu | Val | Val | Ser | Gln | Ala | Met | Gly | Gly | Val | Leu | Leu | Gly | Val | Val | |
| | | | | 355 | | | | | 360 | | | | | 365 | | |

| ttc | acc | gtc | ggg | cgc | aac | gcg | atg | aaa | gtc | ctc | tcc | gag | gaa | gaa | atg | 1152 |
|---|---|---|---|---|---|---|---|---|---|---|---|---|---|---|---|---|
| Phe | Thr | Val | Gly | Arg | Asn | Ala | Met | Lys | Val | Leu | Ser | Glu | Glu | Glu | Met | |
| | 370 | | | | | 375 | | | | | 380 | | | | | |

| aag | tca | acc | gac | ttt | gtc | cag | atg | cag | gtc | ctg | acg | acg | aga | aat | att | 1200 |
|---|---|---|---|---|---|---|---|---|---|---|---|---|---|---|---|---|
| Lys | Ser | Thr | Asp | Phe | Val | Gln | Met | Gln | Val | Leu | Thr | Thr | Arg | Asn | Ile | |
| 385 | | | | | 390 | | | | | 395 | | | | | 400 | |

| gag | ccg | acg | gct | ttc | aat | cgg | tgg | ttc | agc | ggt | ggc | ctc | agc | tac | cag | 1248 |
|---|---|---|---|---|---|---|---|---|---|---|---|---|---|---|---|---|

```
Glu Pro Thr Ala Phe Asn Arg Trp Phe Ser Gly Gly Leu Ser Tyr Gln
                405                 410                 415 att gag cac cac atc tgg cct cag ctg ccc cga cac agc tta ccc aag    1296
Ile Glu His His Ile Trp Pro Gln Leu Pro Arg His Ser Leu Pro Lys
                420                 425                 430 gcg cgc gaa att ctc acc aag ttt tgc agc aag tat gat att ccg tac    1344
Ala Arg Glu Ile Leu Thr Lys Phe Cys Ser Lys Tyr Asp Ile Pro Tyr
            435                 440                 445 gcc agt caa ggc ctc att gaa ggt aac atg gaa gtg tgg aaa atg ctc    1392
Ala Ser Gln Gly Leu Ile Glu Gly Asn Met Glu Val Trp Lys Met Leu
    450                 455                 460 tcg aag ctt ggg gaa tcc cta tag                                    1416
Ser Lys Leu Gly Glu Ser Leu
465                 470
```

<210> SEQ ID NO 43
<211> LENGTH: 471
<212> TYPE: PRT
<213> ORGANISM: Porphyridium cruentum

<400> SEQUENCE: 43

```
Met Ala Pro Asn Val Asp Ser Gly Ser Lys Asp Arg Gly Val Ser Ala
1               5                   10                  15

Val Lys Glu Val Val Ser Gly Ala Thr Ala Asn Ala Leu Ser Pro Ala
            20                  25                  30

Glu Arg Val Val Thr Arg Lys Glu Leu Ala Gly His Ala Ser Arg Glu
        35                  40                  45

Ser Val Trp Ile Ala Val Asn Gly Arg Val Tyr Asp Val Thr Gly Phe
    50                  55                  60

Glu Asn Val His Pro Gly Gly Glu Ile Ile Leu Thr Ala Ala Gly Gln
65                  70                  75                  80

Asp Ala Thr Asp Val Phe Ala Ala Phe His Thr Pro Ala Thr Trp Lys
                85                  90                  95

Met Met Pro Gln Phe Leu Val Gly Asn Leu Glu Glu Asp Ala Leu Ser
            100                 105                 110

Ala Lys Pro Ser Lys Gln Leu Asn Gly His Ser Pro His Glu Tyr Gln
        115                 120                 125

Ala Asp Ile Arg Lys Met Arg Ala Glu Leu Val Lys Leu Arg Ala Phe
    130                 135                 140

Asp Ser Asn Lys Phe Phe Tyr Leu Phe Lys Phe Leu Ser Thr Ser Ala
145                 150                 155                 160

Ile Cys Ala Leu Leu Val Val Met Ala Leu Gly Met Lys Asp Ser Met
                165                 170                 175

Ile Val Thr Ala Leu Ala Ala Phe Thr Met Ala Leu Phe Trp Gln Gln
            180                 185                 190

Cys Gly Trp Leu Ala His Asp Phe Leu His His Gln Val Phe Lys Asn
        195                 200                 205

Arg Val Phe Asn Asn Leu Val Gly Leu Val Val Gly Asn Val Tyr Gln
    210                 215                 220

Gly Phe Ser Val Ser Trp Trp Lys Met Lys His Asn His His Ala
225                 230                 235                 240

Ala Pro Asn Val Thr Ser Thr Ala Ala Gly Pro Asp Pro Asp Ile Asp
                245                 250                 255

Thr Val Pro Val Leu Ser Trp Ser Glu Lys Leu Ile Glu Gly Asp Ser
            260                 265                 270

Lys Glu Met Glu Asp Leu Pro Met Phe Leu Met Lys Asn Gln Lys Ile
        275                 280                 285
```

Phe Tyr Trp Pro Val Leu Cys Val Ala Arg Ile Ser Trp Leu Leu Gln
    290                 295                 300

Ser Leu Leu Phe Gln Arg Ala Pro Val Trp Asn Phe Val Gly Gly Asn
305                 310                 315                 320

Ser Trp Arg Ala Val Glu Thr Val Ala Leu Leu Met His His Gly Ala
            325                 330                 335

Tyr Phe Tyr Leu Leu Ser Leu Leu Lys Ser Trp Val His Val Val Leu
            340                 345                 350

Phe Leu Val Val Ser Gln Ala Met Gly Gly Val Leu Leu Gly Val Val
            355                 360                 365

Phe Thr Val Gly Arg Asn Ala Met Lys Val Leu Ser Glu Glu Glu Met
    370                 375                 380

Lys Ser Thr Asp Phe Val Gln Met Gln Val Leu Thr Thr Arg Asn Ile
385                 390                 395                 400

Glu Pro Thr Ala Phe Asn Arg Trp Phe Ser Gly Gly Leu Ser Tyr Gln
                405                 410                 415

Ile Glu His His Ile Trp Pro Gln Leu Pro Arg His Ser Leu Pro Lys
            420                 425                 430

Ala Arg Glu Ile Leu Thr Lys Phe Cys Ser Lys Tyr Asp Ile Pro Tyr
            435                 440                 445

Ala Ser Gln Gly Leu Ile Glu Gly Asn Met Glu Val Trp Lys Met Leu
450                 455                 460

Ser Lys Leu Gly Glu Ser Leu
465                 470

<210> SEQ ID NO 44
<211> LENGTH: 8502
<212> TYPE: DNA
<213> ORGANISM: Artificial Sequence
<220> FEATURE:
<223> OTHER INFORMATION: Plasmid pY109 #1

<400> SEQUENCE: 44
gtacgagccg gaagcataaa gtgtaaagcc tggggtgcct aatgagtgag ctaactcaca    60
ttaattgcgt tgcgctcact gcccgctttc cagtcgggaa acctgtcgtg ccagctgcat   120
taatgaatcg gccaacgcgc ggggagaggc ggtttgcgta ttgggcgctc ttccgcttcc   180
tcgctcactg actcgctgcg ctcggtcgtt cggctgcggc gagcggtatc agctcactca   240
aaggcggtaa tacggttatc cacagaatca ggggataacg caggaaagaa catgtgagca   300
aaaggccagc aaaaggccag gaaccgtaaa aaggccgcgt tgctggcgtt tttccatagg   360
ctccgccccc ctgacgagca tcacaaaaat cgacgctcaa gtcagaggtg gcgaaacccg   420
acaggactat aaagatacca ggcgtttccc cctggaagct ccctcgtgcg ctctcctgtt   480
ccgaccctgc cgcttaccgg atacctgtcc gcctttctcc cttcgggaag cgtggcgctt   540
tctcatagct cacgctgtag gtatctcagt tcggtgtagg tcgttcgctc caagctgggc   600
tgtgtgcacg aaccccccgt tcagcccgac cgctgcgcct tatccggtaa ctatcgtctt   660
gagtccaacc cggtaagaca cgacttatcg ccactggcag cagccactgg taacaggatt   720
agcagagcga ggtatgtagg cggtgctaca gagttcttga agtggtggcc taactacggc   780
tacactagaa ggacagtatt tggtatctgc gctctgctga gccagttacc ttcggaaaa    840 agagttggta gctcttgatc cggcaaacaa accaccgctg gtagcggtgg ttttttttgtt   900 tgcaagcagc agattacgcg cagaaaaaaa ggatctcaag aagatccttt gatcttttct   960
acggggtctg acgctcagtg gaacgaaaac tcacgttaag ggattttggt catgagatta  1020

```
tcaaaaagga tcttcaccta gatccttttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga gcgcagaagt     1320 ggtcctgcaa ctttatccgc ctccatccag tctattaatt gttgccggga agctagagta    1380
agtagttcgc cagttaatag tttgcgcaac gttgttgcca ttgctacagg catcgtggtg    1440
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
agaagtaagt tggccgcagt gttatcactc atggttatgg cagcactgca taattctctt    1620
actgtcatgc catccgtaag atgcttttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaaagggaat aagggcgaca cggaaatgtt gaatactcat actcttcctt    1980
tttcaatatt attgaagcat ttatcagggt tattgtctca tgagcggata catatttgaa    2040
tgtatttaga aaaataaaca aatagggtt ccgcgcacat ttccccgaaa agtgccacct     2100
gacgcgccct gtagcggcgc attaagcgcg gcgggtgtgg tggttacgcg cagcgtgacc    2160
gctacacttg ccagcgccct agcgcccgct cctttcgctt tcttcccttc ctttctcgcc    2220
acgttcgccg gctttccccg tcaagctcta atcgggggc tccctttagg gttccgattt     2280
agtgctttac ggcacctcga ccccaaaaaa cttgattagg gtgatggttc acgtagtggg    2340
ccatcgccct gatagacggt ttttcgccct ttgacgttgg agtccacgtt ctttaatagt    2400
ggactcttgt tccaaactgg aacaacactc aaccctatct cggtctattc ttttgattta    2460
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatcg gtgcgggcct cttcgctatt acgccagctg gcgaaagggg    2640
gatgtgctgc aaggcgatta agttgggtaa cgccagggtt ttcccagtca cgacgttgta    2700
aaacgacggc cagtgaattg taatacgact cactataggg cgaattgggt accgggcccc    2760
ccctcgaggt cgatggtgtc gataagcttg atatcgaatt catgtcacac aaaccgatct    2820
tcgcctcaag gaaacctaat tctacatccg agagactgcc gagatccagt ctacactgat    2880
taattttcgg gccaataatt taaaaaaatc gtgttatata atattatatg tattatatat    2940
atacatcatg atgatactga cagtcatgtc ccattgctaa atagacagac tccatctgcc    3000
gcctccaact gatgttctca atatttaagg ggtcatctcg cattgtttaa taataaacag    3060
actccatcta ccgcctccaa atgatgttct caaaatatat tgtatgaact tatttttatt    3120
acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
aacagctatt cacacgttac tattgagatt attattggac gagaatcaca cactcaactg    3420
```

```
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag ataiaccaaa gtagcggtat agtggcaatc aaaaagcttc    3600
tctggtgtgc ttctcgtatt tatttttatt ctaatgatcc attaaaggta tatatttatt    3660
tcttgttata taatccttt gtttattaca tgggctggat acataaaggt attttgattt     3720
aattttttgc ttaaattcaa tccccctcg ttcagtgtca actgtaatgg taggaaatta     3780
ccatactttt gaagaagcaa aaaaatgaa agaaaaaaaa aatcgtattt ccaggttaga     3840
cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgttttttt ttgttttttt tttttctaat    4020
gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg ccagagagc ccttgcaaga    4800 cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100 gaggggagc acagtgccgg cgtaggtgaa gtcgtcaatg atgtcgatat gggttttgat    5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg gggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
```

```
ggccgcctag atgacaaatt caacaactca cagctgactt tctgccattg ccactagggg    5880 ggggccttt  tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata     6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc ggggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggcgccgaa    6780
tgtggactcc ggaagcaagg accgcggcgt gagcgcggtc aaagaagtag tctctggcgc    6840
gacggccaac gcgctgagtc cggccgagcg cgtggtgacc aggaaggagc tcgcggggca    6900
cgcctcaagg gagtcggtgt ggattgcggt gaacggccgt gtgtacgatg tgaccggctt    6960
tgagaacgtt caccctggcg gcgagatcat tctgaccgcc gccgggcagg acgcaacgga    7020
cgtgtttgcc gcgtttcaca cgcccgccac gtggaaaatg atgccgcagt tcctcgtggg    7080
aaacctcgag gaggacgcgc tctctgccaa accgtctaag cagcttaatg ggcattcgcc    7140
acacgagtac caagctgata tccgaaagat gcgtgcggaa cttgtcaagc tgcgcgcgtt    7200
cgactcgaac aagttcttct acctgttcaa gttcctgtcc acgtctgcga tttgcgccct    7260
ctcggtggtc atggcgctcg gcatgaagga ctcgatgatc gtcacggcgc tcgccgcgtt    7320
caccatggca ctcttctggc agcagtgcgg ctggctcgca cacgactttc tgcaccatca    7380
ggtgttcaag aacagggtgt tcaacaacct ggtcggtctt gttgttggta atgtctatca    7440
gggcttttcg gtatcctggt ggaagatgaa gcacaaccac caccacgccg ctccaaacgt    7500
gacgtcaacg gccgctgggc cagacccaga catcgacact gtgcccgtgc tcttgtggag    7560
cgagaaactc atcgagggtg atagcaagga gatggaggat ctgcccatgt tcctcatgaa    7620
gaaccagaag atctttact  ggccggttct gtgcgtggcg cgcatcagct ggctcctgca    7680
gagccttctc ttccagcgcg cgccggtctg gaactttgtg ggcggaaaca gctggcgcgc    7740
ggtggagatc gtcgcgcttc tcatgcatca cggcgcctac ttctacttgc tgtccttgct    7800
caagagctgg gtccatgtcg cgctctttt ggtggtgagc caggcgatgg gtggtgtgct     7860
actcggcgtc gtgttcaccg tcgggcacaa cgcgatgaaa gtcctctccg aggaagaaat    7920
gaagtcaacc gactttgtcc agatgcaggt cctgacgacg agaaatattg agccgacggc    7980
tttcaatcgg tggttcagcg gtggcctcag ctaccagatt gagcaccaca tctggcctca    8040
gctgccccga cacagcttac ccaaggcgcg cgaaattctc accaagtttt gcagcaagta    8100
tgatattccg tacgccagtc aaggcctcat tgaaggtaac atggaagtgt ggaaaatgct    8160
ctcgaagctt ggggaatccc tatagggccg caagtgtgga tggggaagtg agtgcccggt    8220
```

| | |
|---|---|
| tctgtgtgca caattggcaa tccaagatgg atggattcaa cacagggata tagcgagcta | 8280 |
| cgtggtggtg cgaggatata gcaacggata tttatgtttg acacttgaga atgtacgata | 8340 |
| caagcactgt ccaagtacaa tactaaacat actgtacata ctcatactcg tacccgggca | 8400 |
| acggtttcac ttgagtgcag tggctagtgc tcttactcgt acagtgtgca atactgcgta | 8460 |
| tcatagtctt tgatgtatat cgtattcatt catgttagtt gc | 8502 |

<210> SEQ ID NO 45
<211> LENGTH: 8502
<212> TYPE: DNA
<213> ORGANISM: Artificial Sequence
<220> FEATURE:
<223> OTHER INFORMATION: Plasmid pY109 #2

<400> SEQUENCE: 45

| | |
|---|---|
| gtacgagccg gaagcataaa gtgtaaagcc tggggtgcct aatgagtgag ctaactcaca | 60 |
| ttaattgcgt tgcgctcact gcccgctttc cagtcgggaa acctgtcgtg ccagctgcat | 120 |
| taatgaatcg gccaacgcgc ggggagaggc ggtttgcgta ttgggcgctc ttccgcttcc | 180 |
| tcgctcactg actcgctgcg ctcggtcgtt cggctgcggc gagcggtatc agctcactca | 240 |
| aaggcggtaa tacggttatc cacagaatca ggggataacg caggaaagaa catgtgagca | 300 |
| aaaggccagc aaaaggccag gaaccgtaaa aaggccgcgt tgctggcgtt tttccatagg | 360 |
| ctccgccccc ctgacgagca tcacaaaaat cgacgctcaa gtcagaggtg gcgaaacccg | 420 |
| acaggactat aaagatacca ggcgtttccc cctggaagct ccctcgtgcg ctctcctgtt | 480 |
| ccgaccctgc cgcttaccgg atacctgtcc gcctttctcc cttcgggaag cgtggcgctt | 540 |
| tctcatagct cacgctgtag gtatctcagt tcggtgtagg tcgttcgctc caagctgggc | 600 |
| tgtgtgcacg aaccccccgt tcagcccgac cgctgcgcct tatccggtaa ctatcgtctt | 660 |
| gagtccaacc cggtaagaca cgacttatcg ccactggcag cagccactgg taacaggatt | 720 |
| agcagagcga ggtatgtagg cggtgctaca gagttcttga agtggtggcc taactacggc | 780 |
| tacactagaa ggacagtatt tggtatctgc gctctgctga gccagttac cttcggaaaa | 840 |
| agagttggta gctcttgatc cggcaaacaa accaccgctg gtagcggtgg tttttttgtt | 900 |
| tgcaagcagc agattacgcg cagaaaaaaa ggatctcaag aagatccttt gatcttttct | 960 |
| acggggtctg acgctcagtg gaacgaaaac tcacgttaag ggattttggt catgagatta | 1020 |
| tcaaaaagga tcttcaccta gatcctttta aattaaaaat gaagttttaa atcaatctaa | 1080 |
| agtatatatg agtaaacttg gtctgacagt taccaatgct taatcagtga ggcacctatc | 1140 |
| tcagcgatct gtctatttcg ttcatccata gttgcctgac tccccgtcgt gtagataact | 1200 |
| acgatacggg agggcttacc atctggcccc agtgctgcaa tgataccgcg agacccacgc | 1260 |
| tcaccggctc cagatttatc agcaataaac cagccagccg gaagggccga gcgcagaagt | 1320 |
| ggtcctgcaa ctttatccgc ctccatccag tctattaatt gttgccggga agctagagta | 1380 |
| agtagttcgc cagttaatag tttgcgcaac gttgttgcca ttgctacagg catcgtggtg | 1440 |
| tcacgctcgt cgtttggtat ggcttcattc agctccggtt cccaacgatc aaggcgagtt | 1500 |
| acatgatccc ccatgttgtg caaaaaagcg gttagctcct tcggtcctcc gatcgttgtc | 1560 |
| agaagtaagt tggccgcagt gttatcactc atggttatgg cagcactgca taattctctt | 1620 |
| actgtcatgc catccgtaag atgcttttct gtgactggtg agtactcaac caagtcattc | 1680 |
| tgagaatagt gtatgcggcg accgagttgc tcttgcccgg cgtcaatacg ggataatacc | 1740 |
| gcgccacata gcagaacttt aaaagtgctc atcattggaa aacgttcttc ggggcgaaaa | 1800 |

```
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aatagggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct ccttttcgctt cttcccttc ctttctcgcc   2220 acgttcgccg gctttccccg tcaagctcta atcgggggc tcccctttagg gttccgattt   2280 agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tattttatt   3120 acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatccttttt gtttattaca tgggctggat acataaaggt attttgattt   3720
aattttttgc ttaaattcaa tccccctcg ttcagtgtca actgtaatgg taggaaatta   3780
ccatactttt gaagaagcaa aaaaaatgaa agaaaaaaaa aatcgtatttt ccaggttaga   3840 cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttacttt agcttatgca   4140 tgctacttgg gtgtaatatt gggatctgtt cggaaatcaa cggatgctca atcgatttcg   4200
```

```
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg ccagagagc ccttgcaaga    4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggccttt tatatggcca agccaagctc tccacgtcgg ttgggctgca cccaacaata   5940
aatgggtagg gttgcaccaa caaagggatg ggatggggg tagaagatac gaggataacg    6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc ccctggata    6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc gggggcttg tctagggtat atataaacag tggctctccc aatcggttgc    6540
cagtctcttt tttcctttct ttccccacag attcgaaatc taaactacac atcacacaat   6600
```

```
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggcgccgaa    6780
tgtggactcc ggaagcaagg accgcggcgt gagcgcggtc aaagaagtag tctctggcgc    6840
gacggccaac gcgctgagtc cggccgagcg cgtggtgacc aggaaggagc tcgcggggca    6900
cgcctcaagg gagtcggtgt ggattgcggt gaacggccgt gtgtacgatg tgaccggctt    6960
tgagaacgtt caccctggcg gcgagatcat tctgaccgcc gccgggcagg acgcaacgga    7020
cgtgtttgcc gcgtttcaca cgcccgccac gtggaaaatg atgccgcagt tcctcgtggg    7080
aaacctcgag gaggacgcgc tctctgccaa accgtctaag cagcttaatg ggcattcgcc    7140
acacgagtac caagctgata tccgaaagat gcgtgcggaa cttgtcaagc tgcgcgcgtt    7200
cgactcgaac aagttcttct acctgttcaa gttcctgtcc acgtctgcga tttgcgccct    7260
cttggtggtc atggcgctcg gcatgaagga ctcgatgatc gtcacggcgc tcgccgcgtt    7320
caccatggca ctcttctggc agcagtgcgg ctggctcgct cacgactttc tgcaccatca    7380
ggtgttcaag aacagggtgt tcaacaacct ggtcggtctt gttgttggta atgtctatca    7440
gggcttttcg gtatcctggt ggaagatgaa gcacaaccac caccacgccg ctccaaacgt    7500
gacgtcaacg gccgctgggc cagacccaga catcgacact gtgcccgtgc tctcgtggag    7560
cgagaaactc atcgagggtg atagcaagga gatggaggat ctgcccatgt tcctcatgaa    7620
gaaccagaag atcttttact ggccggttct gtgcgtggcg cgcatcagct ggctcctgca    7680
gagccttctc ttccagcgcg cgccggtctg gaactttgtg ggcggaaaca gctggcgcgc    7740
ggtggagacc gtcgcgcttc tcatgcatca cggcgcctac ttctacttgc tgtccttgct    7800
caagagctgg gtccatgtcg tgctctttt ggtggtgagc caggcgatgg tggtgtgct    7860 actcggcgtc gtgttcaccg tcgggcgcaa cgcgatgaaa gtcctctccg aggaagaaat    7920
gaagtcaacc gactttgtcc agatgcaggt cctgacgacg agaaatattg agccgacggc    7980
tttcaatcgg tggttcagcg gtggcctcag ctaccagatt gagcaccaca tctggcctca    8040
gctgccccga cacagcttac ccaaggcgcg cgaaattctc accaagttttt gcagcaagta    8100 tgatattccg tacgccagtc aaggcctcat tgaaggtaac atggaagtgt ggaaaatgct    8160
ctcgaagctt ggggaatccc tatagggccg caagtgtgga tggggaagtg agtgcccggt    8220
tctgtgtgca caattggcaa tccaagatgg atggattcaa cacagggata tagcgagcta    8280
cgtggtggtg cgaggatata gcaacggata tttatgtttg acacttgaga atgtacgata    8340
caagcactgt ccaagtacaa tactaaacat actgtacata ctcatactcg tacccgggca    8400
acggtttcac ttgagtgcag tggctagtgc tcttactcgt acagtgtgca atactgcgta    8460
tcatagtctt tgatgtatat cgtattcatt catgttagtt gc                       8502
```

<210> SEQ ID NO 46  
<211> LENGTH: 1426  
<212> TYPE: DNA  
<213> ORGANISM: Porphyridium cruentum  
<220> FEATURE:  
<221> NAME/KEY: CDS  
<222> LOCATION: (3)..(1418)  
<223> OTHER INFORMATION: synthetic delta-6 desaturase (codon-optimized for Yarrowia lipolytica)

<400> SEQUENCE: 46

```
cc atg gct ccc aac gtc gac tcc gga tcg aag gac cga ggc gtg tct       47
   Met Ala Pro Asn Val Asp Ser Gly Ser Lys Asp Arg Gly Val Ser
```

```
                1              5                  10                 15
    gcc gtc aag gag gtg gtc tcc ggt gct act gcc aac gct ctg tct cct         95
    Ala Val Lys Glu Val Val Ser Gly Ala Thr Ala Asn Ala Leu Ser Pro
                    20                  25                  30 gcc gag cga gtt gtc acc cga aag gag ctg gca gga cac gcc tct cga        143
    Ala Glu Arg Val Val Thr Arg Lys Glu Leu Ala Gly His Ala Ser Arg
                35                  40                  45 gaa tcc gtg tgg att gct gtc aac ggc aga gtt tac gat gtt acc gga        191
    Glu Ser Val Trp Ile Ala Val Asn Gly Arg Val Tyr Asp Val Thr Gly
                    50                  55                  60 ttc gag aac gtg cat ccc ggt ggc gag atc att ctc act gcc gct gga        239
    Phe Glu Asn Val His Pro Gly Gly Glu Ile Ile Leu Thr Ala Ala Gly
            65                  70                  75 cag gac gcg acc gat gtc ttt gct gcc ttt cac aca cct gcc acc tgg        287
    Gln Asp Ala Thr Asp Val Phe Ala Ala Phe His Thr Pro Ala Thr Trp
    80                  85                  90                  95 aag atg atg cct cag ttc ctc gtg gga aac ctc gag gaa gac gct ctg        335
    Lys Met Met Pro Gln Phe Leu Val Gly Asn Leu Glu Glu Asp Ala Leu
                        100                 105                 110 tct gcc aag ccc tcc aag cag ctc aat ggt cat tct cca cac gag tac        383
    Ser Ala Lys Pro Ser Lys Gln Leu Asn Gly His Ser Pro His Glu Tyr
                    115                 120                 125 cag gcc gac att cga aag atg cgt gcc gag ctt gtc aag ctg cga gct        431
    Gln Ala Asp Ile Arg Lys Met Arg Ala Glu Leu Val Lys Leu Arg Ala
                130                 135                 140 ttc gat tcc aac aag ttc ttt tac ctg ttc aag ttt ctc tca acc tct        479
    Phe Asp Ser Asn Lys Phe Phe Tyr Leu Phe Lys Phe Leu Ser Thr Ser
            145                 150                 155 gcc atc tgt gcg ctg tcg gtg gtc atg gct ctt ggc atg aag gac tcc        527
    Ala Ile Cys Ala Leu Ser Val Val Met Ala Leu Gly Met Lys Asp Ser
    160                 165                 170                 175 atg att gtc aca gcg ctg gct gcc ttt act atg gca ctc ttc tgg cag        575
    Met Ile Val Thr Ala Leu Ala Ala Phe Thr Met Ala Leu Phe Trp Gln
                        180                 185                 190 caa tgc gga tgg ctg gca cac gac ttt ctt cac cat cag gtc ttc aag        623
    Gln Cys Gly Trp Leu Ala His Asp Phe Leu His His Gln Val Phe Lys
                    195                 200                 205 aac cga gtg ttc aac aat ctg gtc ggt ctc gtt gtc gga aac gtc tac        671
    Asn Arg Val Phe Asn Asn Leu Val Gly Leu Val Val Gly Asn Val Tyr
                210                 215                 220 cag ggc ttt tcg gtg tcc tgg tgg aag atg aaa cac aat cat cac cat        719
    Gln Gly Phe Ser Val Ser Trp Trp Lys Met Lys His Asn His His His
            225                 230                 235 gcc gct ccc aac gtt acg tct act gcc gct gga cca gac ccc gat atc        767
    Ala Ala Pro Asn Val Thr Ser Thr Ala Ala Gly Pro Asp Pro Asp Ile
    240                 245                 250                 255 gac acc gtt cct gtc ctc ttg tgg tcc gag aag ctt atc gaa ggc gat        815
    Asp Thr Val Pro Val Leu Leu Trp Ser Glu Lys Leu Ile Glu Gly Asp
                        260                 265                 270 tcc aag gag atg gaa gac ctt ccc atg ttc ctc atg aag aac cag aaa        863
    Ser Lys Glu Met Glu Asp Leu Pro Met Phe Leu Met Lys Asn Gln Lys
                    275                 280                 285 atc ttc tac tgg cct gtt ctg tgt gtg gct cga atc agc tgg ctg ctt        911
    Ile Phe Tyr Trp Pro Val Leu Cys Val Ala Arg Ile Ser Trp Leu Leu
                290                 295                 300 cag tcc ctg ctc ttt cag cga gca ccc gtc tgg aac ttc gtt ggt ggc        959
    Gln Ser Leu Leu Phe Gln Arg Ala Pro Val Trp Asn Phe Val Gly Gly
            305                 310                 315 aac agc tgg cga gcc gtc gag atc gtt gct ctg ctc atg cac cac gga       1007
    Asn Ser Trp Arg Ala Val Glu Ile Val Ala Leu Leu Met His His Gly
```

```
                320                 325                 330                 335
gcc tac ttc tac ctt ctg tcc ttg ctc aag tct tgg gtc cac gtg gca          1055
Ala Tyr Phe Tyr Leu Leu Ser Leu Leu Lys Ser Trp Val His Val Ala
                340                 345                 350 ctg ttt ctt gtc gtg tcc cag gct atg ggt ggc gtt ctg ctc gga gtc          1103
Leu Phe Leu Val Val Ser Gln Ala Met Gly Gly Val Leu Leu Gly Val
                355                 360                 365 gtg ttc acc gtt ggt cac aac gcc atg aag gtt ctg agc gag gaa gag          1151
Val Phe Thr Val Gly His Asn Ala Met Lys Val Leu Ser Glu Glu Glu
            370                 375                 380 atg aag tct acc gac ttt gtc cag atg caa gtg ctt act acc cga aac          1199
Met Lys Ser Thr Asp Phe Val Gln Met Gln Val Leu Thr Thr Arg Asn
        385                 390                 395 atc gaa ccc aca gcc ttc aac cga tgg ttc agc ggt ggc ctg tcc tat          1247
Ile Glu Pro Thr Ala Phe Asn Arg Trp Phe Ser Gly Gly Leu Ser Tyr
400                 405                 410                 415 cag atc gag cat cac att tgg cct cag ctt ccc aga cac tct ctt ccc          1295
Gln Ile Glu His His Ile Trp Pro Gln Leu Pro Arg His Ser Leu Pro
                420                 425                 430 aag gct cgg gag att ctt acc aag ttc tgc tcc aag tac gac att ccc          1343
Lys Ala Arg Glu Ile Leu Thr Lys Phe Cys Ser Lys Tyr Asp Ile Pro
                435                 440                 445 tac gcc tct caa ggt ctc atc gaa ggc aac atg gag gtc tgg aaa atg          1391
Tyr Ala Ser Gln Gly Leu Ile Glu Gly Asn Met Glu Val Trp Lys Met
            450                 455                 460 ctg tcg aaa ctt ggc gag tcc ctg taa gcggccgc                             1426
Leu Ser Lys Leu Gly Glu Ser Leu
        465                 470

<210> SEQ ID NO 47
<211> LENGTH: 471
<212> TYPE: PRT
<213> ORGANISM: Porphyridium cruentum

<400> SEQUENCE: 47

Met Ala Pro Asn Val Asp Ser Gly Ser Lys Asp Arg Gly Val Ser Ala
1               5                   10                  15

Val Lys Glu Val Val Ser Gly Ala Thr Ala Asn Ala Leu Ser Pro Ala
            20                  25                  30

Glu Arg Val Val Thr Arg Lys Glu Leu Ala Gly His Ala Ser Arg Glu
        35                  40                  45

Ser Val Trp Ile Ala Val Asn Gly Arg Val Tyr Asp Val Thr Gly Phe
    50                  55                  60

Glu Asn Val His Pro Gly Gly Glu Ile Ile Leu Thr Ala Ala Gly Gln
65                  70                  75                  80

Asp Ala Thr Asp Val Phe Ala Ala Phe His Thr Pro Ala Thr Trp Lys
                85                  90                  95

Met Met Pro Gln Phe Leu Val Gly Asn Leu Glu Glu Asp Ala Leu Ser
            100                 105                 110

Ala Lys Pro Ser Lys Gln Leu Asn Gly His Ser Pro His Glu Tyr Gln
        115                 120                 125

Ala Asp Ile Arg Lys Met Arg Ala Glu Leu Val Lys Leu Arg Ala Phe
    130                 135                 140

Asp Ser Asn Lys Phe Phe Tyr Leu Phe Lys Phe Leu Ser Thr Ser Ala
145                 150                 155                 160

Ile Cys Ala Leu Ser Val Val Met Ala Leu Gly Met Lys Asp Ser Met
                165                 170                 175

Ile Val Thr Ala Leu Ala Ala Phe Thr Met Ala Leu Phe Trp Gln Gln
```

```
                180                 185                 190
Cys Gly Trp Leu Ala His Asp Phe Leu His His Gln Val Phe Lys Asn
            195                 200                 205

Arg Val Phe Asn Asn Leu Val Gly Leu Val Val Gly Asn Val Tyr Gln
        210                 215                 220

Gly Phe Ser Val Ser Trp Trp Lys Met Lys His Asn His His His Ala
225                 230                 235                 240

Ala Pro Asn Val Thr Ser Thr Ala Ala Gly Pro Asp Pro Asp Ile Asp
            245                 250                 255

Thr Val Pro Val Leu Leu Trp Ser Glu Lys Leu Ile Glu Gly Asp Ser
        260                 265                 270

Lys Glu Met Glu Asp Leu Pro Met Phe Leu Met Lys Asn Gln Lys Ile
            275                 280                 285

Phe Tyr Trp Pro Val Leu Cys Val Ala Arg Ile Ser Trp Leu Leu Gln
        290                 295                 300

Ser Leu Leu Phe Gln Arg Ala Pro Val Trp Asn Phe Val Gly Gly Asn
305                 310                 315                 320

Ser Trp Arg Ala Val Glu Ile Val Ala Leu Leu Met His His Gly Ala
            325                 330                 335

Tyr Phe Tyr Leu Leu Ser Leu Leu Lys Ser Trp Val His Val Ala Leu
        340                 345                 350

Phe Leu Val Val Ser Gln Ala Met Gly Gly Val Leu Leu Gly Val Val
        355                 360                 365

Phe Thr Val Gly His Asn Ala Met Lys Val Leu Ser Glu Glu Glu Met
        370                 375                 380

Lys Ser Thr Asp Phe Val Gln Met Gln Val Leu Thr Thr Arg Asn Ile
385                 390                 395                 400

Glu Pro Thr Ala Phe Asn Arg Trp Phe Ser Gly Gly Leu Ser Tyr Gln
            405                 410                 415

Ile Glu His His Ile Trp Pro Gln Leu Pro Arg His Ser Leu Pro Lys
        420                 425                 430

Ala Arg Glu Ile Leu Thr Lys Phe Cys Ser Lys Tyr Asp Ile Pro Tyr
        435                 440                 445

Ala Ser Gln Gly Leu Ile Glu Gly Asn Met Glu Val Trp Lys Met Leu
450                 455                 460

Ser Lys Leu Gly Glu Ser Leu
465                 470

<210> SEQ ID NO 48
<211> LENGTH: 5
<212> TYPE: PRT
<213> ORGANISM: Artificial Sequence
<220> FEATURE:
<223> OTHER INFORMATION: Porphyridium cruentum delta-6 desaturase
      His-rich motif

<400> SEQUENCE: 48

His Asp Phe Leu His
1               5

<210> SEQ ID NO 49
<211> LENGTH: 5
<212> TYPE: PRT
<213> ORGANISM: Artificial Sequence
<220> FEATURE:
<223> OTHER INFORMATION: Porphyridium cruentum delta-6 desaturase
      His-rich motif

<400> SEQUENCE: 49
```

His Asn His His His
1               5

<210> SEQ ID NO 50
<211> LENGTH: 5
<212> TYPE: PRT
<213> ORGANISM: Artificial Sequence
<220> FEATURE:
<223> OTHER INFORMATION: Porphyridium cruentum delta-6 desaturase
      His-rich motif

<400> SEQUENCE: 50

Gln Ile Glu His His
1               5

<210> SEQ ID NO 51
<211> LENGTH: 693
<212> TYPE: DNA
<213> ORGANISM: Porphyridium cruentum

<400> SEQUENCE: 51
tggcagcaga tgggctggtt ragccatgac tttctgcacc atcaggtgtt caagaacagg      60
gtgttcaaca acctggtcgg tcttgttgtt ggtaatgtct atcagggctt ttcggtatcc     120
tggtggaaga tgaagcacaa ccaccaccac gccgctccaa acgtgacgtc aacgccgct     180 gggccagacc cagacatcga cactgtgccc gtgctcttgt ggagcgagaa actcatcgag     240
ggtgatagca aggagatgga ggatctgccc atgttcctca tgaagaacca gaagatcttt     300
tactggccgg ttctgtgcgt ggcgcgcatc agctggctcc tgcagagcct tctcttccag     360
cgcgcgccgg tctggaactt tgtgggcgga acagctggc gcgcggtgga gatcgtcgcg      420
cttctcatgc atcacggcgc ctacttctac ttgctgtcct tgctcaagag ctgggtccat     480
gtcgcgctct ttttggtggt gagccaggcg atgggtggtg tgctactcgg cgtcgtgttc     540
accgtcgggc acaacgcgat gaaagtcctc tccgaggaag aaatgaagtc aaccgacttt     600
gtccagatgc aggtcctgac gacgagaaat attgagccga cggctttcaa tcggtggttc     660
agcggyggct tcagctacca gatygagcac cac                                   693

<210> SEQ ID NO 52
<211> LENGTH: 410
<212> TYPE: DNA
<213> ORGANISM: Porphyridium cruentum

<400> SEQUENCE: 52
cctacttcta cttgctgtcc ttgctcaaga gctgggtcca tgtcgcgctc ttttggtgg      60 tgagccaggc gatgggtggt gtgctactcg gcgtcgtgtt caccgtcggg cacaacgcga     120
tgaaagtcct ctccgaggaa gaaatgaagt caaccgactt tgtccagatg caggtcctga     180
cgacgagaaa tattgagccg acggctttca atcggtggtt cagcggtggc ctcagctacc     240
agattgagca ccacatctgg cctcagctgc cccgacacag cttacccaag gcgcgcgaaa     300
ttctcaccaa gttttgcagc aagtatgata ttccgtacgc cagtcaaggc ctcattgaag     360
gtaacatgga agtgtggaaa atgctctcga agcttgggga atccctatag                 410

<210> SEQ ID NO 53
<211> LENGTH: 822
<212> TYPE: DNA
<213> ORGANISM: Porphyridium cruentum

<400> SEQUENCE: 53

-continued

```
atggcgccga atgtggactc cggaagcaag gaccgcggcg tgagcgcggt caaagaagta    60
gtctctggcg cgacgccaa cgcgctgagt ccggccgagc gcgtggtgac caggaaggag    120
ctcgcgggc acgcctcaag ggagtcggtg tggattgcgg tgaacggccg tgtgtacgat    180
gtgaccggct ttgagaacgt tcaccctggc ggcgagatca ttctgaccgc cgccgggcag   240
gacgcaacgg acgtgtttgc cgcgtttcac acgcccgcca cgtggaaaat gatgccgcag   300
ttcctcgtgg gaaacctcga ggaggacgcg ctctctgcca aaccgtctaa gcagcttaat   360
gggcattcgc cacacgagta ccaagctgat atccgaaaga tgcgtgcgga acttgtcaag   420
ctgcgcgcgt tcgactcgaa caagttcttc tacctgttca agttcctgtc cacgtctgcg   480
atttgcgccc tctcggtggt catggcgctc ggcatgaagg actcgatgat cgtcacggcg   540
ctcgccgcgt tcaccatggc actcttctgg cagcagtgcg gctggctcgc acacgacttt   600
ctgcaccatc aggtgttcaa gaacagggtg ttcaacaacc tggtcggtct tgttgttggt   660
aatgtctatc agggcttttc ggtatcctgg tggaagatga agcacaacca ccaccacgcc   720
gctccaaacg tgacgtcaac ggccgctggg ccagacccag acatcgacac tgtgcccgtg   780
ctcttgtgga gcgagaaact catcgagggt gatagcaagg ag                     822
```